US006455674B1

(12) United States Patent
Einat et al.

(10) Patent No.: US 6,455,674 B1
(45) Date of Patent: Sep. 24, 2002

(54) HYPOXIA-REGULATED GENES

(75) Inventors: Paz Einat; Rami Skaliter, both of Nes Ziona (IL)

(73) Assignee: Quark Biotech, Inc., Pleasanton, CA (US)

( * ) Notice: Subject to any disclaimer, the term of this patent is extended or adjusted under 35 U.S.C. 154(b) by 0 days.

(21) Appl. No.: 09/604,978

(22) Filed: Jun. 28, 2000

Related U.S. Application Data

(62) Division of application No. 09/138,112, filed on Aug. 21, 1998.
(60) Provisional application No. 60/056,453, filed on Aug. 21, 1997.

(51) Int. Cl.⁷ .............................................. C07K 14/00
(52) U.S. Cl. ...................................................... 530/350
(58) Field of Search ......................................... 530/350

(56) References Cited

U.S. PATENT DOCUMENTS

| | | |
|---|---|---|
| 3,791,993 A | 2/1974 | Schurrs et al. |
| 3,838,153 A | 9/1974 | Schurrs et al. |
| 3,850,572 A | 11/1974 | Schurrs et al. |
| 3,850,578 A | 11/1974 | McConnell |
| 3,853,987 A | 12/1974 | Dreyer |
| 3,867,517 A | 2/1975 | Ling |
| 3,879,262 A | 4/1975 | Schurrs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,666,828 A | 5/1987 | Gusella |
| 4,683,202 A | 7/1987 | Mullis |
| 4,736,866 A | 4/1988 | Leder et al. |
| 4,801,531 A | 1/1989 | Frossard |
| 4,866,042 A | 9/1989 | Neuwelt |
| 4,873,191 A | 10/1989 | Wagner et al. |
| 4,879,219 A | 11/1989 | Wands et al. |
| 5,011,771 A | 4/1991 | Bellet et al. |
| 5,175,383 A | 12/1992 | Leder et al. |
| 5,175,384 A | 12/1992 | Krimpenfort et al. |
| 5,175,385 A | 12/1992 | Wagner et al. |
| 5,192,659 A | 3/1993 | Simons |
| 5,221,778 A | 6/1993 | Byrne et al. |
| 5,225,347 A | 7/1993 | Goldberg et al. |
| 5,272,057 A | 12/1993 | Smulson |
| 5,281,521 A | 1/1994 | Trojanowski et al. |
| 5,288,846 A | 2/1994 | Quertermous et al. |
| 5,298,422 A | 3/1994 | Schwartz et al. |
| 5,347,075 A | 9/1994 | Sorge |
| 5,360,735 A | 11/1994 | Weinshank et al. |
| 5,387,742 A | 2/1995 | Cordell |
| 5,464,764 A | 11/1995 | Capechhi et al. |
| 5,487,992 A | 1/1996 | Capecchi et al. |
| 5,614,396 A | 3/1997 | Bradley et al. |

FOREIGN PATENT DOCUMENTS

| | | |
|---|---|---|
| WO | 93/01420 | 7/1993 |
| WO | 94/06908 | 3/1994 |
| WO | 94/23049 | 10/1994 |
| WO | 94/28123 | 12/1994 |

OTHER PUBLICATIONS

Herman J. C. Berendsen, A Glimpse of the Holy Grail?, Science vol. 282, Oct. 23, 1998, pp. 642–643.

Michael Y. Galperin et al., Who's your neighbor? New computational approaches for functional genomics, Nature Biotechnology, vol. 18, Jun. 2000, pp. 609–613.

Teresa K. Attwood, The Babel of Bioinformatics, Science vol. 290, Oct. 20, 2000, pp. 471–473.

Agrawal, "Antisense oligonucleotides: toward clinical trials", *Trends Biotechnol.* 14(10):376–387 (1996).

Akhter et al, "Interactions of antisense DNA oligonucleotide analogs with phospholipid membranes (liposomes)", *Nuc. Res.* 19:5551–5559 (1991).

Alon et al., "Vascular endothelial growth factor acts as a survival factor for newly formed retinal vessels and has implications for retinopathy of prematurity", *Nat. Med.* 1(10):1024–1028 (1995).

Benjamin et al, "Conditional switching of vascular endothelial growth factor (VEGF) expression in tumors: induction of endothelial cell shedding and regression of hemangioblastoma–like vessels by VEGF withdrawal", *Proc. Natl. Acad. Sci. USA* 94(16):8761–8766 (1997).

Blaesse, Gene Therapy for Cancer, *Sci. Am.* 276(6):111–115 (1997).

Bouck et al, "How tumors become angiogenic" *Adv. Cancer Res.* 69:135–174 (1996).

Bunn et al, "Oxygen sensing and molecular adaptation in hypoxia", *Phgysiol. Rev.* 76:839–885 (1996).

Burke et al, "Preparation of Clone Libraries in Yeast Artificial–Chromosome Vectors", in *Methods in Enzymology*, vol. 194, "Guide to Yeast Genetics and Molecular Biology", eds. Guthrie et al, Academic Press, Inc. Chap. 17, pp. 251–270 (1991).

Calabretta et al, "Antisense strategies in the treatment of leukemias", *Semin. Oncol.* 23:78 (1996).

Capecchi, "Altering the genome by homologous recombination", *Science* 244:1288–1292 (1989).

Carmeliet et al, "Role of HIF–1alpha in hypoxia–mediated apoptosis, cell proliferation and tumour angiogenesis", *Nature* 349(66923):485–490 (1998).

Crooke, "Progress in antisense therapeutics", *Hematol. Pathol.* 2:59 (1995).

(List continued on next page.)

*Primary Examiner*—Andrew Wang
(74) *Attorney, Agent, or Firm*—Browdy and Neimark, P.L.L.C.

(57) ABSTRACT

Isolated hypoxia-regulated polypeptides have sequences as set forth in SEQ ID NO:9, SEQ ID NO:10, SEQ ID NO:7 and SEQ ID NO:11. Antibodies directed against such polypeptides may be prepared.

3 Claims, 5 Drawing Sheets

OTHER PUBLICATIONS

Davies Et al, "Targeted alterations in yeast artificial chromosomes for inter–species gene transfer", *Nucleic Acids Research* 20(11):2693–2698 (1992).

de Gruyter, *Concise Encyclopedia Biology*, p. 32.

Dickinson et al, "High frequency gene targeting using insertional vectors", *Human Molecular Genetics* 2(8):1299–1302 (1993).

Duff et al, "Insertion of a pathogenic mutation into a yeast artificial chromosome containing the human APP gene and expression in ES cells", *Research Advances in Alzheimer's Disease and Related Disorders* (1995).

Duke et al, "Cell Suicide in Health and Disease", *Sci. Am.*, pp. 80–87 (1996).

Eckstein, "Nucleotide Phosphorothioates", *Ann. Rev. Biochme.* 54:367–402 (1985).

Felgner, "Nonviral Strategies for Gene Therapy", *Sci. Am.*, pp. 102–106 (1997).

Fyodorov et al, et–1, a novel ETS domain factor that can activate neuronal nAchR gene transcription, *J. Neurobiol.* 34(2):151–163 (1998).

Gallagher et al, "Identification of p53 Genetic Suppressor Elements which Confer Resistance to Cisplatin", *Oncogene* 14:185–193 (1997).

Gewritz, "Oligodeoxynucleotide–based therapeutics for human leukemias", *Stem Cells Dayt.* 11:96 (1993).

Gordon, Transgenic Animals, *Int. Rev. Cytol.* 115:171–229 (1989).

Hanahan et al, "Patterns and Emerging Mechanisms of Angiogenic Switch During Tumorigenesis" *Cell* 86:353–364 (1996).

Hanania et al, "Recent advances in the application of gene therapy to human disease", *Am. J. Med.* 99:537 (1995).

Herskowitz, "Functional Inactivation of Genes by Dominant Negative Mutations", *Nature* 329(6136):219–222 (1987).

Holzmayer et al, "Isolation of Dominant Negative Mutants and Inhibitory Antisense RNA Sequences by Expression Selection of Random DNA Fragments", *Nucleic Acids Res.* 20(4):711–717 (1992).

Huxley et al, "The human HPRT gene on a yeast artificial chromosome is functional when transferred to mouse cells by cell fusion", *Genomics* 9:742–750 (1991).

Iyer et al, *J. Org. Chem.* 55:4693–4699 (1990).

Jakobovits et al, "Germ–line transmission and expression of a human–derived yeast artificial chromosome", *Nature* 362:255–261 (1993).

Lamb et al, "Introduction and expression of the 400 kilobase precursor amyloid protein gene in transgenic mice", *Nature Genetics* 5:22–29 (1993).

Lavitrano et al, "Sperm cells as vectors for introducing foreign DNA into eggs: genetic transformation of mice", *Cell* 57:717–723 (1989).

Lefebvre–d'Hellencourt et al, "Immunomodulation by cytokine antisense oligonucleotides" *Eur. Cytokine Netw.* 6:7 (1995).

Lev–Lehman et al, "Antisense Oligomers in vitro and in vivo", in *Antisense Therapeutics,* Cohen et al, ed., Plenum Press (New York, 1997)s.

Lo, *Mol. Cell. Biol.* 3:1803–1814 (1983).

Loke et al, "Characterization of oligonucleotide transport into living cells", *Proc. Natl. Acad. Sci. USA* 86:3474 (1989).

Mansour, "Gene targeting in murine embryonic stem cells: Introduction of specific alterations into the mammalian genome", *GATA* 7(8):219–227 (1990).

Morrison, "Suppression of basic fibroblast growth factor expression by antisense oligonucleotides inhibits the growth of transformed human astrocytes", *J. biol. Chem.* 266:728 (1991).

Niinaka et al, "Expression and secretion of neuroleukin/phosphohexose isomerase/maturation factor as autocrine motility factor by tumor cells", *Cancer Res.* 58(12):2667–2674 (1998).

Pearson et al, "Expression of the human β–amyloid precursor protein gene from a yeast artificial chromosome in transgenic mice", *Proc. Nat. Acad. Sci. USA* 90:10578–10582 (1993).

Rosolen et al, "Antisense inhibition of single copy N–myc expression results in decreased cell growth without reduction of c–myc protein in a neuroepithelioma cell line", *Cancer Res.* 50:6316–6322 (1990).

Rothstein, "Targeting, disruption, replacement, and allele rescue: integrative DNA transformation in yeast", in *Methods in Enzymology,* vol. 194, "Guide to Yeast Genetics and Molecular Biology", Guthrie et al, eds., Academic Press, Inc. (1991), Chapt. 19, pp. 281–301.

Scanlon et al, "Oligonucleotides–mediated modulation of mammalian gene expression", *FASEB J.* 9:1288 (1995).

Schedl et al, "A yeast artificial chromosome covering the tyrosinase gene confers copy number–dependent expression in transgenic mice", *Nature* 362:258–261 (1993).

Shaw et al, "Modified deoxyoligonucleotides stable to exonuclease degradation in serum", *Nucleic Acids Res.* 19:747–750 (1991).

Spitzer et al, "Inhibition of deoxynucleases by phosphorothioate groups in oligodeoxyribonucleotides", *Nucleic Acids Res.* 18:11691–11704 (1988).

Strauss et al, "Germ line transmission of a yeast artificial chromosome spanning the murine alpha 1(I) collagen locus", *Science* 259:1904–1907 (1993).

Thompson et al, "Germ line transmission and expression of a corrected HPRT gene produced by gene targeting in embryonic stem cells", *Cell* 56:313–321 (1989).

Uhlmann et al, "Antisense Oligonucleotides: A New Therapeutic Principle", *Chem. Rev.* 90(4):543–584 (1990).

Van der Putten et al, "Efficient insertion of genes into the mouse germ line via retroviral vectors", *Proc Natl Acad Sci U S A.* 82(18):6148–6152 (1985).

Wagner et al, "Potent and selective inhibition of gene expression by an antisense heptanucleotide", *Nature Biotechnology* 14:840–844 (1996).

Wagner, "Gene inhibition using antisense oligodeoxynucleotides", *Nature* 372:333 (1994).

Watanabe et al, "Tumor cell autocrine motility factor is the neuroleukin/phosphohexose isomerase polypeptide", *Cancer Res.* 56(13):2960–2963 (1996).

Whitesell et al, "Episome–generated N–myc antisense RNA restricts the differentiation potential of primitive neuroectodermal cell liens", *Mol. Cell. Biol.* 11:1360 (1991).

Wright et al, "Antisense Molecules and Their Potential for the Treatment of Cancer and AIDs", *Cancer J.* 8:185–189 (1995).

Woolf et al, "The stability, toxicity and effectiveness of unmodified and phosphorothioate antisense oligodeoxynucleotides in Xenopus oocytes and embryos", *Nucleic Acids Res.* 18:1763–1769 (1989).

Yakubov et al, "Mechanism of oligonucleotide uptake by cells: involvement of specific receptors?", *Proc Natl Acad Sci U S A* 86(17):6454–6458 (1989).

HYPOXIA-REGULATED GENES

The present application is a division of U.S. application Ser. No. 09/138,112, filed Aug. 21, 1998, which is the non-provisional application of U.S. application No. 60/056,453, filed Aug. 21, 1997, now abandoned.

BACKGROUND OF THE INVENTION

1. Field of the Invention

Identification of genes that are differentially expressed in hypoxia and use of the genes and gene products for diagnosis and therapeutic intervention.

2. Description of the Related Art

The level of tissue oxygenation plays an important role in normal development as well as in pathologic processes such as ischemia. Tissue oxygenation plays a significant regulatory role in both apoptosis and in angiogenesis (Bouck et al, 1996; Bunn et al, 1996; Dor et al, 1997; Carmeliet et al, 1998). Apoptosis (see Duke et al, 1996 for review) and growth arrest occur when cell growth and viability are reduced due to oxygen deprivation (hypoxia). Angiogenesis (i.e. blood vessel growth, vascularization), is stimulated when hypooxygenated cells secrete factors which stimulate proliferation and migration of endothelial cells in an attempt to restore oxygen homeostasis (for review see Hanahan et al, 1996).

Ischemic disease pathologies involve a decrease in the blood supply to a bodily organ, tissue or body part generally caused by constriction or obstruction of the blood vessels as for example retinopathy, acute renal failure, myocardial infarction and stroke. Therefore apoptosis and angiogenesis as induced by the ischemic condition are also involved in these disease states. Neoangiogenesis is seen in some forms of retinopathy and in tumor growth. It is recognized that angiogenesis is necessary for tumor growth and that retardation of angiogenesis would be a useful tool in controlling malignancy and retinopathies. Further, it would be useful to induce tumorigenic cells to undergo apoptosis (i.e. programmed cell death).

However, these processes are complex cascades of events controlled by many different genes reacting to the various stresses such as hypoxia. Expression of different genes reacting to the hypoxic stress can trigger not only apoptosis or angiogenesis but both. In cancer it has been observed that apoptosis and angiogenesis related genes are therapeutic targets. However, hypoxia itself plays a critical role in the selection of mutations that contribute to more severe tumorigenic phenotypes (Graeber et al., 1996). Therefore identifying candidate genes and gene products that can be utilized therapeutically not only in cancer and ischemia and that may either induce apoptosis or angiogenesis or to retard the processes is needed. It would be useful to identify genes that have direct causal relationships between a disease and its related pathologies and an up- or down-regulator (responder) gene.

SUMMARY OF THE INVENTION

According to the present invention, purified, isolated and cloned nucleic acid sequences encoding hypoxia-responding genes which have sequences as set is forth in the group comprising SEQ ID No:1, SEQ ID No:2, SEQ ID No:3, SEQ ID No:4 and SEQ ID No:5 or a complementary or allelic variation sequence and human homologs as needed thereto. The present invention further provides proteins as encoded by the nucleic acid sequences as set forth in SEQ ID No:1, SEQ ID No:2, SEQ ID No:3, SEQ ID No:4, SEQ ID No:5 and SEQ ID No:6 with SEQ ID Nos:7–11 being exemplars of the proteins. The present invention further provides antibodies directed against the proteins as encoded by the nucleic acid sequences as set forth in SEQ ID No:1, SEQ ID No:2, SEQ No:3, SEQ ID No:4, SEQ ID No:5 and SEQ ID No:6 including SEQ ID Nos:7–11.

The present invention further provides transgenic animals and cell lines carrying at least one of the expressible nucleic acid sequences as set forth in SEQ ID No:1, SEQ ID No:2, SEQ ID No:3, SEQ ID No:4, SEQ ID No:5 and SEQ ID No:6. The present invention further provides knock-out eucaryotic organisms in which at least one of the nucleic acid sequences as set forth in SEQ ID No:1, SEQ ID No:2, SEQ ID No:3, SEQ ID No:4, SEQ ID No:5 and SEQ ID No:6 is knocked-out.

The present invention provides a method of regulating angiogenesis in a patient in need of such treatment by administering to a patient a therapeutically effective amount of an antagonist of at least one protein as encoded by the nucleic acid sequences as set forth in SEQ ID No:2, SEQ ID No:3, SEQ ID No:4, SEQ ID No:5 and SEQ ID No:6. Alternatively, the present invention provides a method of regulating angiogenesis in a patient in need of such treatment by administering to a patient a therapeutically effective amount of at least one antisense oligonucleotide against the nucleic acid sequences as set forth in SEQ ID No:2, SEQ ID No:3, SEQ ID No:4, SEQ ID No:5 and SEQ ID No:6 or a dominant negative peptide directed against the sequences or their proteins.

The present invention further provides a method of regulating angiogenesis or apoptosis in a patient in need of such treatment by administering to a patient a therapeutically effective amount of a protein encoded by SEQ ID Nos:2–6 or the protein sequences as set forth in SEQ ID Nos:7–8, 10–11 as active ingredients in a pharmaceutically acceptable carrier.

The present invention provides a method of providing an apoptotic regulating gene by administering directly to a patient in need of such therapy utilizing gene therapy an expressible vector comprising expression control sequences operably linked to one of the sequences set forth in the group comprising SEQ ID NO:2; SEQ ID No:3; SEQ ID No:4; SEQ ID No:5 and SEQ ID No:6 (human homolog).

The present invention also provides a method of providing an angiogenesis regulating gene utilizing gene therapy by administering directly to a patient in need of such therapy an expressible vector comprising expression control sequences operably linked to one of the sequences set forth in the group comprising SEQ ID No:2; SEQ ID No:3; SEQ ID No:4; SEQ ID No:5 and SEQ ID No:6.

The present invention provides a method of regulating response to hypoxic conditions in a patient in need of such treatment by administering to a patient a therapeutically effective amount of an antisense oligonucleotide directed against at least one of the sequences set forth in the group comprising SEQ ID No:2; SEQ ID No:3; SEQ ID No:4; SEQ ID No:5; and SEQ ID No:6. The present invention further provides a method of providing a hypoxia regulating gene utilizing gene therapy by administering directly to a patient in need of such therapy an expressible vector comprising expression control sequences operably linked to one of the sequences set forth in the group comprising SEQ ID No:2; SEQ ID No:3; SEQ ID No:4; SEQ ID No:5 and SEQ ID No:6.

The present invention also provides a method of diagnosing the presence of ischemia in a patient including the steps of analyzing a bodily fluid or tissue sample from the patient for the presence or gene product of at least one expressed gene (up-regulated) as set forth in the group comprising SEQ ID No:2; SEQ ID No:3; SEQ ID No:4; SEQ ID No:5; and SEQ ID No:6 and where ischemia is determined if the up-regulated gene or gene product is ascertained.

DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
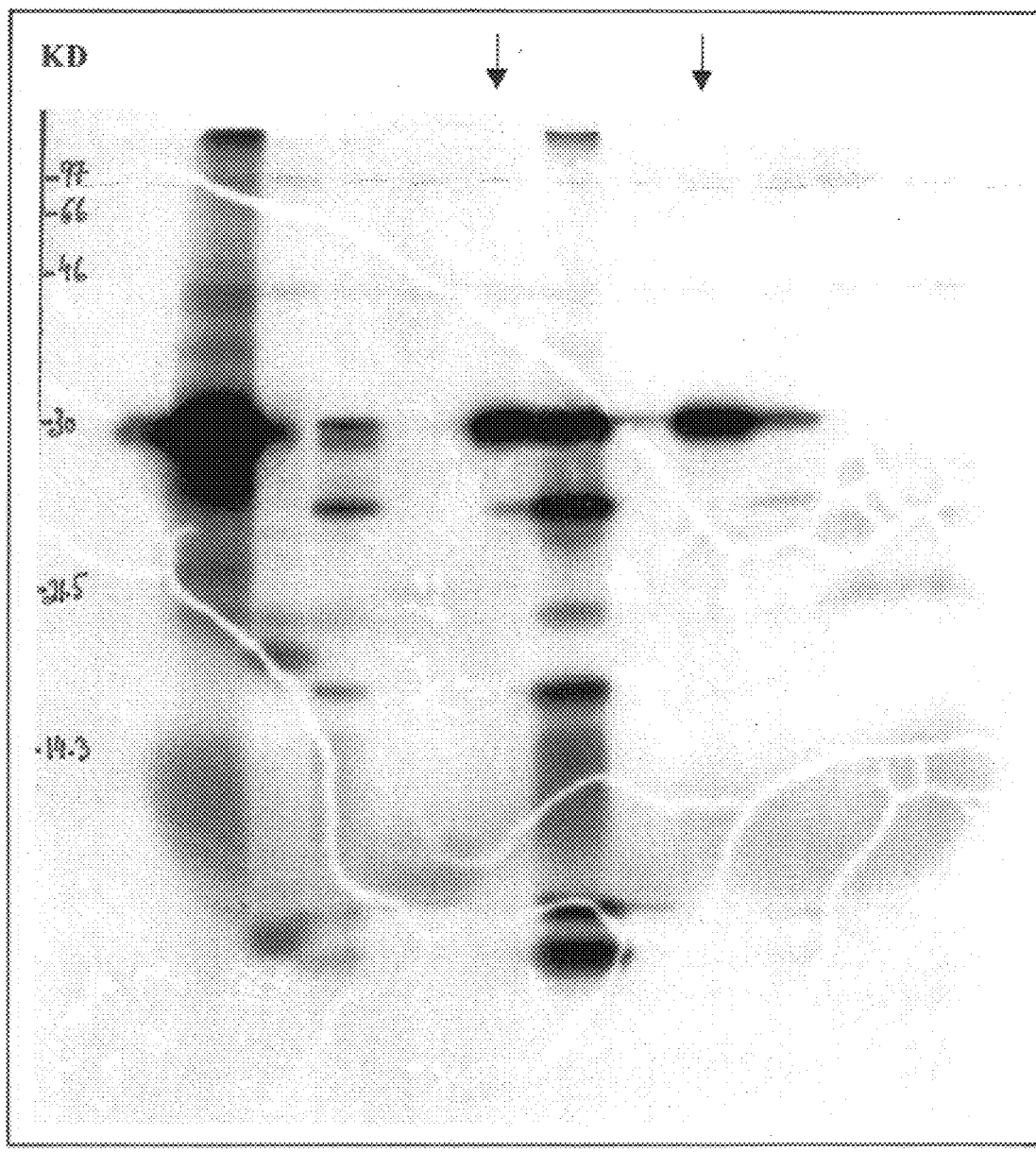
FIG. 1 is a computer scan showing in-vitro translation of Full length cDNA clones of RTP801 (SEQ ID No:1). cDNA clones were translated in-vitro in using a coupled transcription translation kit (Promega). Translation products were separated on acrylamide gel and exposed to X-ray film. Two clones, marked with arrows, gave the expected protein size of approximately 30 KD. This confirms the sequence analysis of the putative reading frame.
Figure 2:
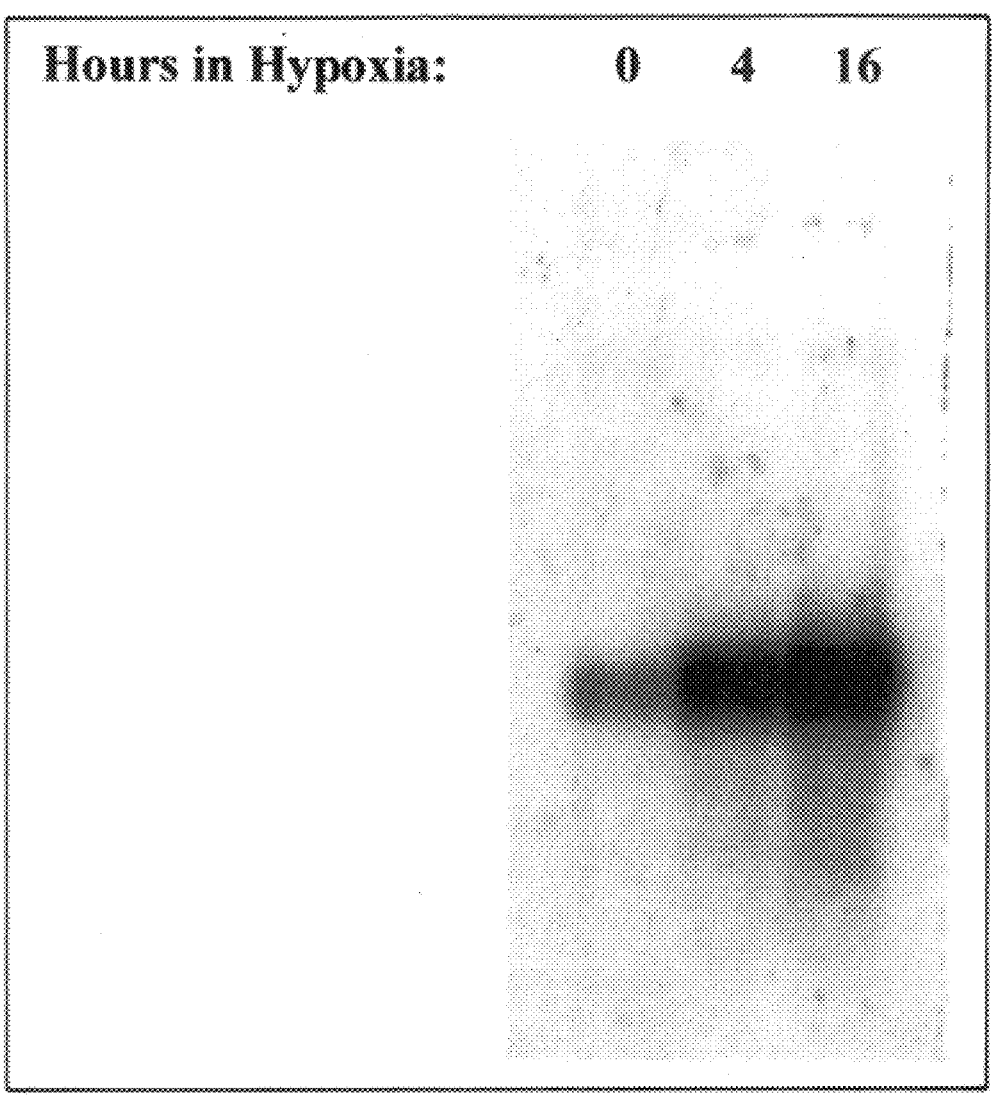
FIG. 2 is a computer scan showing RTP801 (SEQ ID No:1) Northern blot analysis. RNA was extracted from Rat C6 glioma cells which were exposed to hypoxia for 0, 4, or 16 hours. PolyA+ selected mRNA (2 µg) from each sample were separated on denaturing agarose gels, blotted onto Nytran membranes and hybridized with rtp801 probe. One band of 1.8 Kb is observed showing a marked induction after hypoxia.
Figure 3:
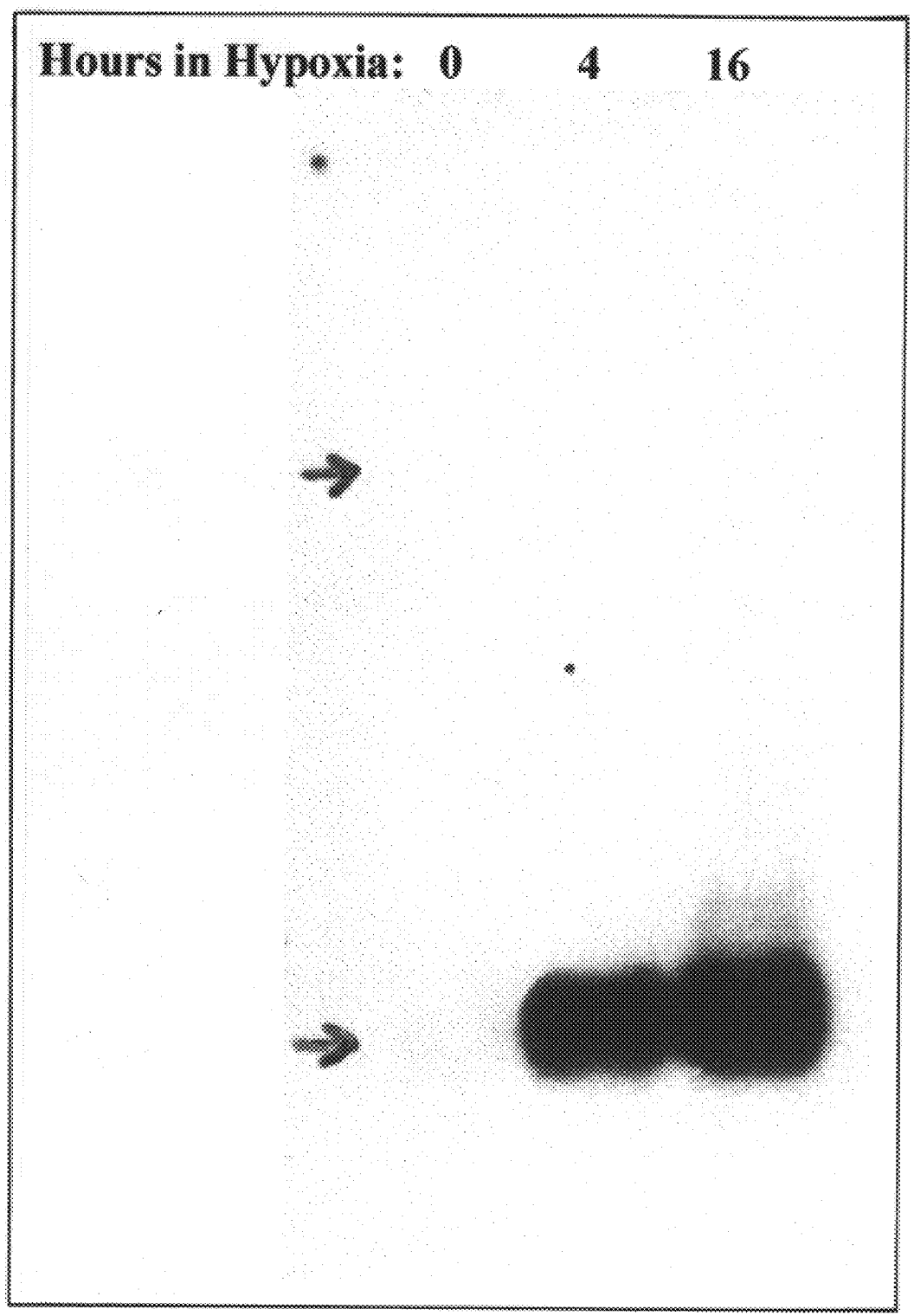
FIG. 3 is a computer scan showing RTP779 (SEQ ID No:2) Northern blot analysis. RNA was extracted from Rat C6 glioma cells which were exposed to hypoxia for 0, 4, or 16 hours. PolyA+ selected mRNA (2 ug) from each sample were separated on denaturing agarose gels, blotted onto Nytran membranes and hybridized with rtp779 probe. One band of 1.8 Kb is observed showing extreme differential expression.
Figure 4:
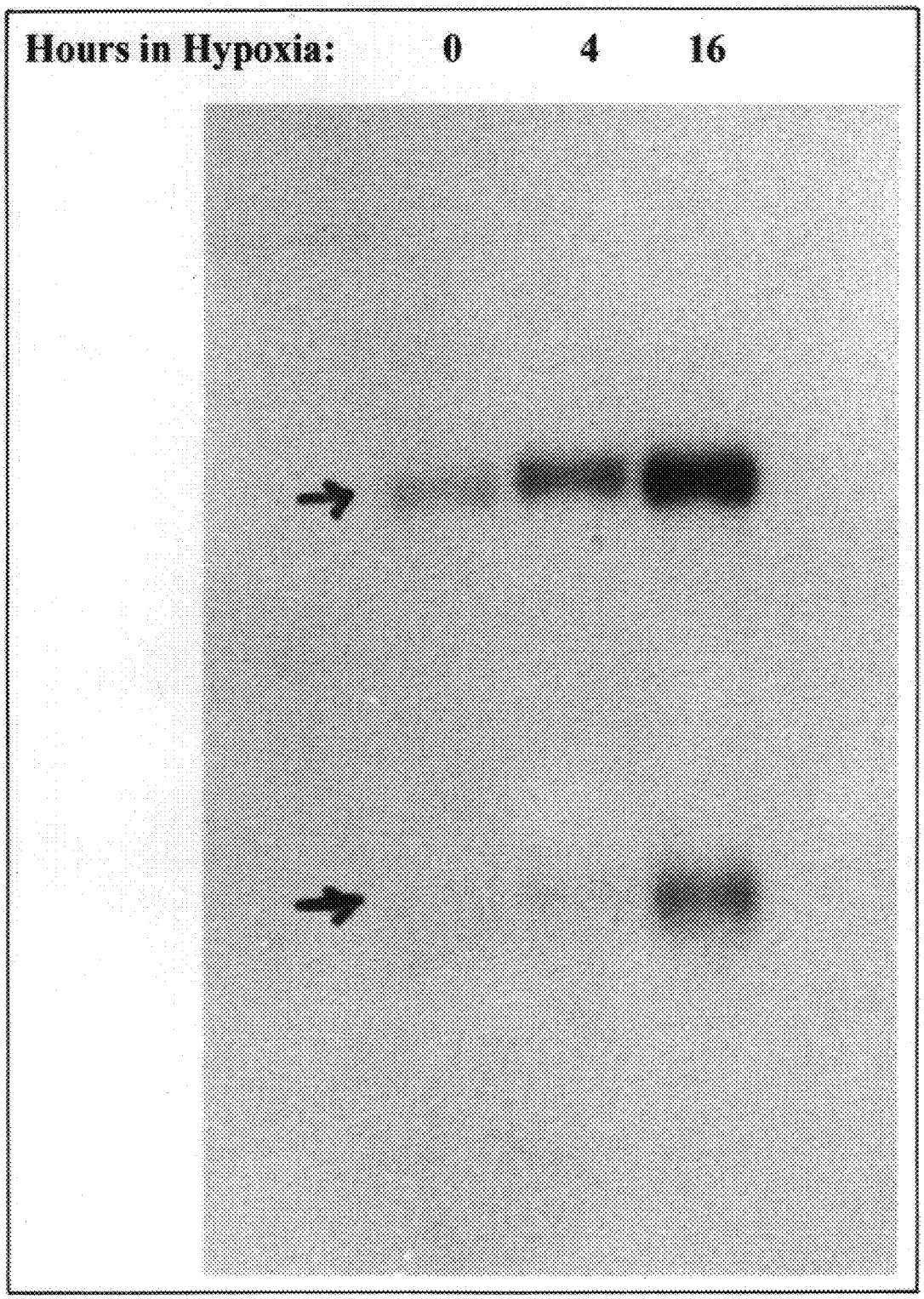
FIG. 4 is a computer scan showing RTP241 (SEQ ID No:3) Northern blot analysis. RNA was extracted from Rat C6 glioma cells which were exposed to hypoxia for 0, 4, or 16 hours. PolyA+ selected mRNA (2 ug) from each sample were separated on denaturing agarose gels, blotted onto Nytran membranes and hybridized with rtp241 probe. Two bands of 1.8 Kb and 4 Kb are observed, both show good differential expression.
Figure 5:
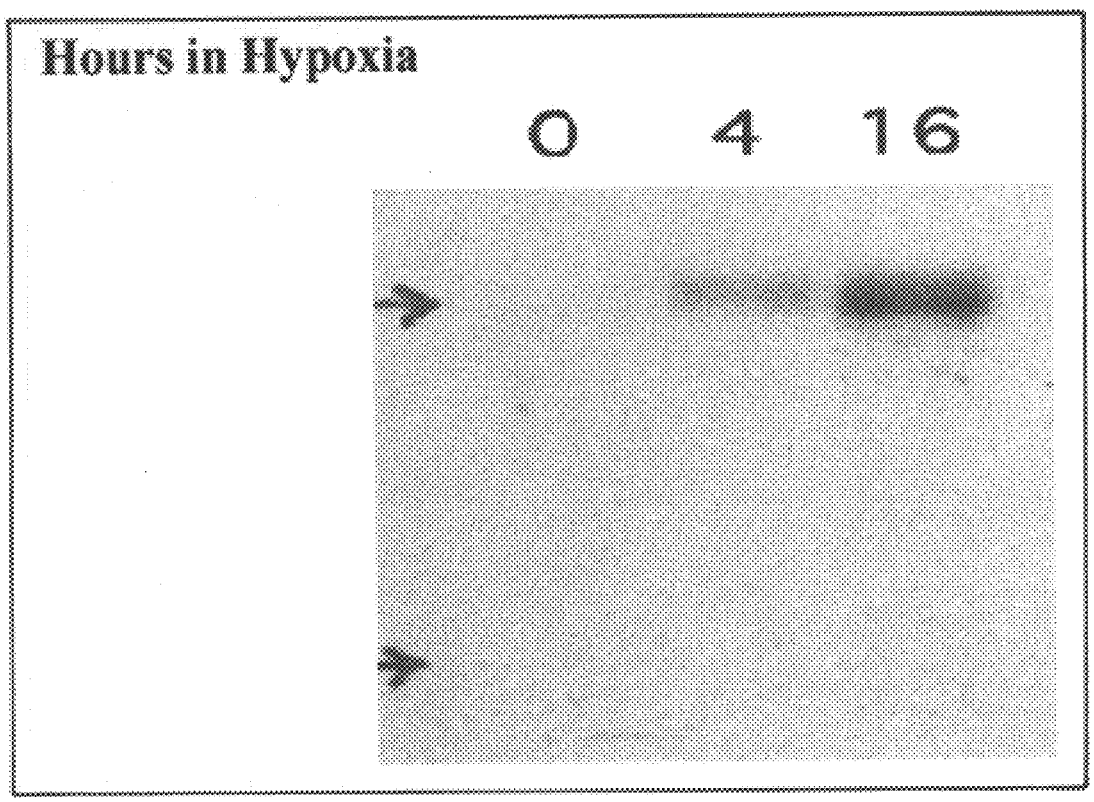
FIG. 5 is a computer scan showing RTP359 (SEQ ID No:5) Northern blot analysis. RNA was extracted from Rat C6 glioma cells which were exposed to hypoxia for 0, 4, or 16 hours. PolyA+ selected mRNA (2 ug) from each sample were separated on denaturing agarose gels, blotted onto Nytran membranes and hybridized with rtp359 probe. One band of 4.5 Kb is observed showing good differential expression.

The present invention identifies candidate genes and gene products that can be utilized therapeutically and diagnostically not only in hypoxia and ischemia and that may regulate apoptosis or angiogenesis. By regulate or modulate or control is meant that the process is either induced or inhibited to the degree necessary to effect a change in the process and the associated disease state in the patient. Whether induction or inhibition is being contemplated will be apparent from the process and disease being treated and will be known to those skilled in the medical arts. The present invention identifies genes for gene therapy, diagnostic and therapeutics that have direct causal relationships between a disease and its related pathologies and up- or down-regulator (responder) genes. That is the present invention is initiated by a physiological relationship between cause and effect.

The present invention provides purified, isolated and cloned nucleic acid polynucleotides (sequences) encoding genes which respond at least to hypoxic conditions by up-regulation of expression and which have sequences as set forth in the group comprising SEQ ID No:1, SEQ ID No:2, SEQ ID No:3, SEQ ID No:4 and SEQ ID No:5 and their analogues and polymorphisms or a complementary or allelic variation sequence thereto. The present invention further provides SEQ ID No:6 which is a known gene (neuroleukin) which also responds to the stress of hypoxia by being up-regulated. SEQ ID No:6 is the human sequence for neuroleukin and has over 90% homology with the rat sequence. The human homolog is used where appropriate. Because of the high homology between the rat and human sequences the rat sequence can also be used for probes and the like as necessary.

The present invention further provides proteins and their analogues as encoded by the nucleic acid sequences as set forth in SEQ ID No:1, SEQ ID No:2, SEQ ID No:3, SEQ ID No:4, SEQ ID No:5 with SEQ ID Nos:7 and 8 as well as SEQ ID Nos:9–11 being exemplars of the proteins. The present invention further provides a method of regulating angiogenesis or apoptosis in a patient in need of such treatment by administering to a patient a therapeutically effective amount of a protein encoded by SEQ ID Nos:2–6 or the protein sequences as set forth in SEQ ID Nos:7–8, 10–11 as active ingredients in a pharmaceutically acceptable carrier.

The proteins may be produced recombinantly (see generally Marshak et al, 1996 "Strategies for Protein is Purification and Characterization. A laboratory course manual." CSHL Press) and analogues may be due to post-translational processing. The term Analogue as used herein is defined as a nucleic acid sequence or protein which has some differences in their amino acid/nucleotide sequences as compared to the native sequence of SEQ ID Nos:1–8. Ordinarily, the analogue will be generally at least 70% homologous over any portion that is functionally relevant. In more preferred embodiments the homology will be at least 80% and can approach 95% homology to the protein/nucleotide sequence. The amino acid or nucleotide sequence of an analog may differ from that of the primary sequence when at least one residue is deleted, inserted or substituted, but the protein or nucleic acid molecule remains functional. Differences in glycosylation can provide protein analogues.

Functionally relevant refers to the biological property of the molecule and in this context means an in vivo effector or antigenic function or activity that is directly or indirectly performed by a naturally occurring protein or nucleic acid molecule. Effector functions include but are not limited to receptor binding, any enzymatic activity or enzyme modulatory activity, any carrier binding activity, any hormonal activity, any activity in promoting or inhibiting adhesion of cells to extracellular matrix or cell surface molecules, or any structural role as well as having the nucleic acid sequence encode functional protein and be expressible. The antigenic functions essentially mean the possession of an epitope or antigenic site that is capable of cross-reacting with antibodies raised against a naturally occurring protein. Biologically active analogues share an effector function of the native which may, but need not, in addition possess an antigenic function.

The present invention further provides antibodies directed against the proteins as encoded by the nucleic acid sequences as set forth in SEQ ID No:1, SEQ ID No:2, SEQ ID No:3, SEQ ID No:4, SEQ ID No:5 and SEQ ID No:6 which can be used in immunoassays and the like.

The antibodies may be either monoclonal, polyclonal or recombinant. Conveniently, the antibodies may be prepared against the immunogen or portion thereof for example a synthetic peptide based on the sequence, or prepared recombinantly by cloning techniques or the natural gene product and/or portions thereof may be isolated and used as the immunogen. Immunogens can be used to produce antibodies by standard antibody production technology well known to those skilled in the art as described generally in Harlow and Lane, *Antibodies: A Laboratory Manual,* Cold Spring Harbor Laboratory, Cold Spring Harbor, N.Y., 1988 and Borrebaeck, *Antibody Engineering—A Practical Guide,* W. H. Freeman and Co., 1992. Antibody fragments may also be prepared from the antibodies and include Fab, F(ab')$_2$, and Fv by methods known to those skilled in the art.

For producing polyclonal antibodies a host, such as a rabbit or goat, is immunized with the immunogen or immunogen fragment, generally with an adjuvant and, if necessary, coupled to a carrier; antibodies to the immunogen are collected from the sera. Further, the polyclonal antibody can be absorbed such that it is monospecific. That is, the sera can be absorbed against related immunogens so that no cross-reactive antibodies remain in the sera rendering it monospecific.

For producing monoclonal antibodies the technique involves hyperimmunization of an appropriate donor with the immunogen, generally a mouse, and solation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

For producing recombinant antibody (see generally Huston et al, 1991; Johnson and Bird, 1991; Mernaugh and Mernaugh, 1995), messenger RNAs from antibody producing B-lymphocytes of animals, or hybridoma are reverse-transcribed to obtain complimentary DNAs (cDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries.

The antibody can be bound to a solid support substrate or conjugated with a detectable moiety or be both bound and conjugated as is well known in the art. (For a general discussion of conjugation of fluorescent or enzymatic moieties see Johnstone & Thorpe, *Immunochemistry in Practice,* Blackwell Scientific Publications, Oxford, 1982.) The binding of antibodies to a solid support substrate is also well known in the art. (See for a general discussion Harlow & Lane *Antibodies: A Laboratory Manual,* Cold Spring Harbor Laboratory Publications, New York, 1988 and Borrebaeck, *Antibody Engineering—A Practical Guide,* W. H. Freeman and Co., 1992.) The detectable moieties contemplated with the present invention can include, but are not limited to, fluorescent, metallic, enzymatic and radioactive markers such as biotin, gold, ferritin, alkaline phosphatase, β-galactosidase, peroxidase, urease, fluorescein, rhodamine, tritium, $^{14}$C and iodination.

The present invention further provides transgenic animals and cell lines carrying at least one expressible nucleic acid sequence as set forth in SEQ ID No:1, SEQ ID No:2, SEQ ID No:3, SEQ ID No:4, SEQ ID No:5 and SEQ ID No:6. By expressible is meant the inclusion with the sequence of all regulatory elements necessary for the expression of the gene or by the placing of the gene in the target genome so that it is expressed. The present invention further provides knock-out eucaryotic organisms in which at least one nucleic acid sequences as set forth in SEQ ID No:1, SEQ ID No:2, SEQ ID No:3, SEQ ID No:4, SEQ ID No:5 and SEQ ID No:6 is knocked-out.

These transgenics and knock-outs are constructed using standard methods known in the art and as set forth in U.S. Pat. Nos. 5,487,992, 5,464,764, 5,387,742, 5,360,735, 5,347,075, 5,298,422, 5,288,846, 5,221,778, 5,175,385, 5,175,384, 5,175,383, 4,736,866 as well as Burke and Olson (1991), Capecchi (1989), Davies et al. (1992), Dickinson et al. (1993), Duff and Lincoln (1995), Huxley et al. (1991), Jakobovits et al. (1993), Lamb et al. (1993), Pearson and Choi (1993), Rothstein (1991), Schedl et al. (1993), Strauss et al. (1993). Further, patent applications WO 94/23049, WO 93/14200, WO 94/06908, WO 94/28123 also provide information.

More specifically, any techniques known in the art may be used to introduce the transgene expressibly into animals to produce the parental lines of animals. Such techniques include, but are not limited to, pronuclear microinjection (U.S. Pat. No. 4,873,191); retrovirus mediated gene transfer into germ lines (Van der Putten et al., 1985); gene targeting in embryonic stem cells (Thompson et al., 1989; Mansour, 1990 and U.S. Pat. No. 5,614,396); electroporation of embryos (Lo, 1983); and sperm-mediated gene transfer (Lavitrano et al., 1989). For a review of such techniques see Gordon (1989).

Further, one parent strain instead of carrying a direct human transgene may have the homologous endogenous gene modified by gene targeting such that it approximates the transgene. That is, the endogenous gene has been "humanized" and/or mutated (Reaume et al, 1996). It should be noted that if the animal and human sequence are essentially homologous a "humanized" gene is not required. The transgenic parent can also carry an overexpressed sequence, either the nonmutant or a mutant sequence and humanized or not as required. The term transgene is therefore used to refer to all these possibilities.

Additionally, cells can be isolated from the offspring which carry a transgene from each transgenic parent and that are used to establish primary cell cultures or cell lines as is known in the art.

Where appropriate, a parent strain will be homozygous for the transgene. Additionally, where appropriate, the endogenous nontransgene in the genome that is homologous to the transgene will be nonexpressive. By nonexpressive is meant that the endogenous gene will not be expressed and that this nonexpression is heritable in the offspring. For example, the endogenous homologous gene could be "knocked-out" by methods known in the art. Alternatively, the parental strain that receives one of the transgenes could carry a mutation at the endogenous homologous gene rendering it nonexpressed.

The present invention provides a method of regulating angiogenesis in a patient in need of such treatment by administering to a patient a therapeutically effective amount of an antagonist of at least one protein as encoded by the nucleic acid sequences as set forth in SEQ ID No:1, SEQ ID No:2, SEQ ID No:3, SEQ ID No:4, SEQ ID No:5 and SEQ ID No:6. The antagonist is dosed and delivered in a pharmaceutically acceptable carrier as described herein below. The term antagonist or antagonizing is used in its broadest sense. Antagonism can include any mechanism or treatment which results in inhibition, inactivation, blocking or reduction in gene activity or gene product. It should be noted that the inhibition of a gene or gene product may provide for an increase in a corresponding function that the gene or gene product was regulating. The antagonizing step can include blocking cellular receptors for the gene products of SEQ ID Nos:1–6 and can include antisense treatment as discussed herein below.

The present invention further provides a method of regulating angiogenesis or apoptosis in a patient in need of such treatment by administering to a patient a therapeutically effective amount of a regulating agent for a protein selected from the group consisting of SEQ ID Nos:7–11 in a pharmaceutically acceptable carrier. The regulating agent is dosed and delivered in a pharmaceutically acceptable carrier as described herein below. For example, a patient may be in need of inducing apoptosis in tumorigenic cells or angiogenesis in trauma situations where for example a limb must be reattached or in a transplant where revascularization is needed.

The present invention provides a method of regulating angiogenesis, or apoptosis in a patient in need of such treatment by administering to a patient a therapeutically effective amount of at least one antisense oligonucleotide or dominant negative peptide (either as cDNA or peptide; Herskowitz, 1987) directed against the nucleic acid sequences as set forth in SEQ ID No:1, SEQ ID No:2, SEQ ID No:3, SEQ ID No:4, SEQ ID No:5 and SEQ ID No:6. The present invention also provides a method of regulating response to hypoxic conditions in a patient in need of such treatment by administering to a patient a therapeutically effective amount of an antisense oligonucleotide directed against at least one of the sequences set forth in the group comprising SEQ ID No:1; SEQ ID No:2; SEQ ID No:3; SEQ ID No:4; SEQ ID No:5; and SEQ ID No:6. The antisense oligonucleotide as the active ingredient in a pharmaceutical composition is dosed and delivered in a pharmaceutically acceptable carrier as discussed herein below.

Many reviews have covered the main aspects of antisense (AS) technology and its enormous therapeutic potential (Wright and Anazodo, 1995). There are reviews on the chemical (Crooke, 1995; Uhlmann et al, 1990), cellular (Wagner, 1994) and therapeutic (Hanania, et al, 1995; Scanlon, et al, 1995; Gewirtz, 1993) aspects of this rapidly developing technology. Within a relatively short time, ample information has accumulated about the in vitro use of AS nucleotide sequences in cultured primary cells and cell lines as well as for in vivo administration of such nucleotide sequences for suppressing specific processes and changing body functions in a transient manner. Further, enough experience is now available in vitro and in vivo in animal models and human clinical trials to predict human efficacy.

Antisense intervention in the expression of specific genes can be achieved by the use of synthetic AS oligonucleotide sequences (for recent reports see Lefebvre-d'Hellencourt et al, 1995; Agrawal, 1996; Lev-Lehman et al, 1997). AS oligonucleotide sequences may be short sequences of DNA, typically 15–30 mer but may be as small as 7 mer (Wagner et al, 1996), designed to complement a target mRNA of interest and form an RNA:AS duplex. This duplex formation can prevent processing, splicing, transport or translation of the relevant mRNA. Moreover, certain AS nucleotide sequences can elicit cellular RNase H activity when hybridized with their target mRNA, resulting in mRNA degradation (Calabretta et al, 1996). In that case, RNase H will cleave the RNA component of the duplex and can potentially release the AS to further hybridize with additional molecules of the target RNA. An additional mode of action results from the interaction of AS with genomic DNA to form a triple helix which may be transcriptionally inactive.

The sequence target segment for the antisense oligonucleotide is selected such that the sequence exhibits suitable energy related characteristics important for oligonucleotide duplex formation with their complementary templates, and shows a low potential for self-dimerization or self-complementation [Anazodo et al., 1996]. For example, the computer program OLIGO (Primer Analysis Software, Version 3.4), can be used to determine antisense sequence melting temperature, free energy properties, and to estimate potential self-dimer formation and self-complimentary properties. The program allows the determination of a qualitative estimation of these two parameters (potential self-dimer formation and self-complimentary) and provides an indication of "no potential" or "some potential" or "essentially complete potential". Using this program target segments are generally selected that have estimates of no potential in these parameters. However, segments can be used that have "some potential" in one of the categories. A balance of the parameters is used in the selection as is known in the art. Further, the oligonucleotides are also selected as needed so that analogue substitution do not substantially affect function.

Phosphorothioate antisense oligonucleotides do not normally show significant toxicity at concentrations that are effective and exhibit sufficient pharmacodynamic half-lives in animals (Agrawal et al., 1996) and are nuclease resistant. Antisense induced loss-of-function phenotypes related with cellular development were shown for the glial fibrillary acidic protein (GFAP), for the establishment of tectal plate formation in chick (Galileo et al., 1991) and for the N-myc protein, responsible for the maintenance of cellular heterogeneity in neuroectodermal cultures (epithelial vs. neuroblastic cells, which differ in their colony forming abilities, tumorigenicity and adherence) (Rosolen et al., 1990; Whitesell et al, 1991). Antisense oligonucleotide inhibition of basic fibroblast growth factor (bFgF), having mitogenic and angiogenic properties, suppressed 80% of growth in glioma cells (Morrison, 1991) in a saturable and specific manner. Being hydrophobic, antisense oligonucleotides interact well with phospholipid membranes (Akhter et al., 1991). Following their interaction with the cellular plasma membrane, they are actively (or passively) transported into living cells (Loke et al., 1989), in a saturable mechanism predicted to involve specific receptors (Yakubov et al., 1989).

Instead of an antisense sequence as discussed herein above, ribozymes may be utilized. This is particularly necessary in cases where antisense therapy is limited by stoichiometric considerations (Sarver et al., 1990, Gene Regulation and Aids, pp. 305–325). Ribozymes can then be used that will target the same sequence. Ribozymes are RNA molecules that possess RNA catalytic ability (see Cech for review) that cleave a specific site in a target RNA. The number of RNA molecules that are cleaved by a ribozyme is greater than the number predicted by stoichiochemistry. (Hampel and Tritz, 1989; Uhlenbeck, 1987).

Ribozymes catalyze the phosphodiester bond cleavage of RNA. Several ribozyme structural families have been identified including Group I introns, RNase P, the hepatitis delta virus ribozyme, hammerhead ribozymes and the hairpin ribozyme originally derived from the negative strand of the tobacco ringspot virus satellite RNA (sTRSV) (Sullivan, 1994; U.S. Pat. No. 5,225,347, columns 4–5). The latter two families are derived from viroids and virusoids, in which the ribozyme is believed to separate monomers from oligomers created during rolling circle replication (Symons, 1989 and 1992). Hammerhead and hairpin ribozyme motifs are most commonly adapted for trans-cleavage of mRNAs for gene therapy (Sullivan, 1994). The ribozyme type utilized in the present invention is selected as is known in the art. Hairpin ribozymes are now in clinical trial and are the preferred type. In general the ribozyme is from 30–100 nucleotides in length.

Modifications or analogues of nucleotides can be introduced to improve the therapeutic properties of the nucleotides. Improved properties include increased nuclease resistance and/or increased ability to permeate cell membranes.

Nuclease resistance, where needed, is provided by any method known in the art that does not interfere with biological activity of the antisense oligodeoxy-nucleotides, cDNA and/or ribozymes as needed for the method of use and delivery (Iyer et al., 1990; Eckstein, 1985; Spitzer and Eckstein, 1988; Woolf et al., 1990; Shaw et al., 1991). Modifications that can be made to oligonucleotides in order to enhance nuclease resistance include modifying the phosphorous or oxygen heteroatom in the phosphate backbone. These include preparing methyl phosphonates, phosphorothioates, phosphorodithioates and morpholino oligomers. In one embodiment it is provided by having phosphorothioate bonds linking between the four to six 3'-terminus nucleotide bases. Alternatively, phosphorothioate bonds link all the nucleotide bases. Other modifications known in the art may be used where the biological activity is retained, but the stability to nucleases is substantially increased.

The present invention also includes all analogues of, or modifications to, an oligonucleotide of the invention that does not substantially affect the function of the oligonucleotide. The nucleotides can be selected from naturally occurring or synthetic modified bases. Naturally occurring bases include adenine, guanine, cytosine, thymine and uracil. Modified bases of the oligonucleotides include xanthine, hypoxanthine, 2-aminoadenine, 6-methyl, 2-propyl and other alkyl adenines, 5-halo uracil, 5-halo cytosine, 6-aza cytosine and 6-aza thymine, psuedo uracil, 4-thiuracil, 8-halo adenine, 8-aminoadenine, 8-thiol adenine, 8-thioalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine.

In addition, analogues of nucleotides can be prepared wherein the structure of the nucleotide is fundamentally altered and that are better suited as therapeutic or experimental reagents. An example of a nucleotide analogue is a peptide nucleic acid (PNA) wherein the deoxyribose (or ribose) phosphate backbone in DNA (or RNA is replaced with a polyamide backbone which is similar to that found in peptides. PNA analogues have been shown to be resistant to degradation by enzymes and to have extended lives in vivo and in vitro. Further, PNAs have been shown to bind stronger to a complementary DNA sequence than a DNA molecule. This observation is attributed to the lack of charge repulsion between the PNA strand and the DNA strand. Other modifications that can be made to oligonucleotides include polymer backbones, cyclic backbones, or acyclic backbones.

The active ingredients of the pharmaceutical composition can include oligonucleotides that are nuclease resistant needed for the practice of the invention or a fragment thereof shown to have the same effect targeted against the appropriate sequence(s) and/or ribozymes. Combinations of active ingredients as disclosed in the present invention can be used including combinations of antisense sequences.

The antisense oligonucleotides (and/or ribozymes) and cDNA of the present invention can be synthesized by any method known in the art for ribonucleic or deoxyribonucleic nucleotides. For example, an Applied Biosystems 380B DNA synthesizer can be used. When fragments are used, two or more such sequences can be synthesized and linked together for use in the present invention.

The nucleotide sequences of the present invention can be delivered either directly or with viral or non-viral vectors. When delivered directly the sequences are generally rendered nuclease resistant. Alternatively the sequences can be incorporated into expression cassettes or constructs such that the sequence is expressed in the cell as discussed herein below. Generally the construct contains the proper regulatory sequence or promoter to allow the sequence to be expressed in the targeted cell.

Negative dominant peptide refers to a partial cDNA sequence that encodes for a part of a protein, i.e. a peptide (see Herskowitz, 1987). This peptide can have a different function from the protein it was derived from. It can interact with the full protein and inhibit its activity or it can interact with other proteins and inhibit their activity in response to the full protein. Negative dominant means that the peptide is able to overcome the natural proteins and fully inhibit their activity to give the cell a different characteristics like resistance or sensitization to killing. For therapeutic intervention either the peptide itself is delivered as the active ingredient of a pharmaceutical composition or the cDNA can be delivered to the cell utilizing the same methods as for antisense delivery.

The present invention provides a method of providing an apoptotic regulating gene, angiogenesis regulating gene or a hypoxia regulating gene by administering directly to a patient in need of such therapy utilizing gene therapy an expressible vector comprising expression control sequences operably linked to one of the sequences set forth in the group comprising SEQ ID No:1; SEQ ID No:2; SEQ ID No:3; SEQ ID No:4; SEQ ID No:5; and SEQ ID No:6.

By gene therapy as used herein refers to the transfer of genetic material (e.g., DNA or RNA) of interest into a host to treat or prevent a genetic or acquired disease or condition phenotype. The genetic material of interest encodes a product (e.g., a protein, polypeptide, peptide, functional RNA, antisense) whose production in vivo is desired. For example, the genetic material of interest can encode a hormone, receptor, enzyme, polypeptide or peptide of therapeutic value. Alternatively, the genetic material of interest encodes a suicide gene. For a review see, in general, the text "Gene Therapy" (Advances in Pharmacology 40, Academic Press, 1997).

Two basic approaches to gene therapy have evolved: (1) ex vivo and (2) in vivo gene therapy. In ex vivo gene therapy cells are removed from a patient, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to express the transfected genetic material in situ.

In in vivo gene therapy, target cells are not removed from the subject rather the genetic material to be transferred is introduced into the cells of the recipient organism in situ, that is within the recipient. In an alternative embodiment, if the host gene is defective, the gene is repaired in situ [Culver, 1998]. These genetically altered cells have been shown to express the transfected genetic material in situ.

The gene expression vehicle is capable of delivery/transfer of heterologous nucleic acid into a host cell. The expression vehicle may include elements to control targeting, expression and transcription of the nucleic acid in a cell selective manner as is known in the art. It should be noted that often the 5'UTR and/or 3'UTR of the gene may be replaced by the 5'UTR and/or 3'UTR of the expression vehicle. Therefore as used herein the expression vehicle may, as needed, not include the 5'UTR and/or 3'UTR of the actual gene to be transferred and only include the specific amino acid coding region.

The expression vehicle can include a promoter for controlling transcription of the heterologous material and can be either a constitutive or inducible promoter to allow selective transcription. Enhancers that may be required to obtain necessary transcription levels can optionally be included. Enhancers are generally any non-translated DNA sequence which works contiguously with the coding sequence (in cis) to change the basal transcription level dictated by the promoter. The expression vehicle can also include a selection gene as described herein below.

Vectors can be introduced into cells or tissues by any one of a variety of known methods within the art. Such methods can be found generally described in Sambrook et al., *Molecular Cloning: A Laboratory Manual,* Cold Springs Harbor Laboratory, New York (1989, 1992), in Ausubel et al., *Current Protocols in Molecular Biology,* John Wiley and Sons, Baltimore, Md. (1989), Chang et al., *Somatic Gene Therapy,* CRC Press, Ann Arbor, Mich. (1995), Vega et al., *Gene Targeting,* CRC Press, Ann Arbor, Mich. (1995), *Vectors: A Survey of Molecular Cloning Vectors and Their Uses,* Butterworths, Boston Mass. (1988) and Gilboa et al (1986) and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods.

Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

A specific example of DNA viral vector for introducing and expressing recombinant sequences is the adenovirus derived vector Adenop53TK. This vector expresses a herpes virus thymidine kinase (TK) gene for either positive or negative selection and an expression cassette for desired recombinant sequences. This vector can be used to infect cells that have an adenovirus receptor which includes most cancers of epithelial origin as well as others. This vector as well as others that exhibit similar desired functions can be used to treat a mixed population of cells and can include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the antibiotic ganciclovir. Negative selection is therefore a means by which infection can be controlled because it provides inducible suicide through the addition of antibiotic. Such protection ensures that if, for example, mutations arise that produce altered forms of the viral vector or recombinant sequence, cellular transformation will not occur.

Features that limit expression to particular cell types can also be included. Such features include, for example, promoter and regulatory elements that are specific for the desired cell type.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention will depend on desired cell type to be targeted and will be known to those skilled in the art. For example, if breast cancer is to be treated then a vector specific for such epithelial cells would be used. Likewise, if diseases or pathological conditions of the hematopoietic system are to be treated, then a viral vector that is specific for blood cells and their precursors, preferably for the specific type of hematopoietic cell, would be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

The recombinant vector can be administered in several ways. If viral vectors are used, for example, the procedure can take advantage of their target specificity and consequently, do not have to be administered locally at the diseased site. However, local administration can provide a quicker and more effective treatment, administration can also be performed by, for example, intravenous or subcutaneous injection into the subject. Injection of the viral vectors into a spinal fluid can also be used as a mode of administration, especially in the case of neuro-degenerative diseases. Following injection, the viral vectors will circulate until they recognize host cells with the appropriate target specificity for infection.

An alternate mode of administration can be by direct inoculation locally at the site of the disease or pathological condition or by inoculation into the vascular system supplying the site with nutrients or into the spinal fluid. Local administration is advantageous because there is no dilution effect and, therefore, a smaller dose is required to achieve expression in a majority of the targeted cells. Additionally, local inoculation can alleviate the targeting requirement required with other forms of administration since a vector can be used that infects all cells in the inoculated area. If expression is desired in only a specific subset of cells within the inoculated area, then promoter and regulatory elements that are specific for the desired subset can be used to accomplish this goal. Such non-targeting vectors can be, for example, viral vectors, viral genome, plasmids, phagemids and the like. Transfection vehicles such as liposomes can also be used to introduce the non-viral vectors described above into recipient cells within the inoculated area. Such transfection vehicles are known by one skilled within the art.

The pharmaceutical. compositions containing the active ingredients of the present invention as described herein above are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the medical arts. The amount must be effective to achieve improvement including but not limited to improved survival rate or more rapid recovery, or improvement or elimination of symptoms and other indicators as are selected as appropriate measures by those skilled in the medical arts. The pharmaceutical compositions can be combinations of the active ingredients but will include at least one active ingredient.

In the method of the present invention, the pharmaceutical compositions of the present invention can be administered in various ways taking into account the nature of compounds in the pharmaceutical compositions. It should be noted that they can be administered as the compound or as pharmaceutically acceptable salt and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

It is noted that humans are treated generally longer than the mice or other experimental animals exemplified herein which treatment has a length proportional to the length of the disease process and drug effectiveness. The doses may be single doses or multiple doses over a period of several days, but single doses are preferred.

The doses may be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological formulation of the compound utilized in the present invention can be administered orally to the patient. Conventional methods such as administering the compounds in tablets, suspensions, solutions, emulsions, capsules, powders, syrups and the like are usable. Known techniques which deliver it orally or intravenously and retain the biological activity are preferred.

In one embodiment, the compound of the present invention can be administered initially by intravenous injection to bring blood levels to a suitable level. The patient's levels are then maintained by an oral dosage form, although other forms of administration, dependent upon the patient's condition and as indicated above, can be used. The quantity to be administered will vary for the patient being treated and will vary from about 100 ng/kg of body weight to 100 mg/kg of body weight per day and preferably will be from 10 μg/kg to 10 mg/kg per day.

The present invention also provides a method of diagnosing the presence of ischemia in a patient including the steps of analyzing a bodily fluid or tissue sample from the patient for the presence or gene product of at least one expressed gene (up-regulated) as set forth in the group comprising SEQ ID No:1; SEQ ID No:2; SEQ ID No:3; SEQ ID No:4; SEQ ID No:5; and SEQ ID No:6 or proteins as set forth in SEQ ID Nos:7–11 and where ischemia is determined if the up-regulated gene or gene product is ascertained as described herein in the Example. The bodily fluids may include tears, serum, urine, sweat or other bodily fluid where secreted proteins from the tissue that is undergoing an ischemic event may be localized. Additional methods for identification of the gene or gene product are immunoassays, such as and ELISA or radioimmunoassays (RIA), can be used as are known to those in the art particularly to identify gene products in the samples. Immunohistochemical staining of tissue samples is also utilized for identification. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521. Further for identification of the gene, in situ hybridization, Southern blotting, single strand conformational polymorphism, restriction endonuclease fingerprinting (REF), PCR amplification and DNA-chip analysis using nucleic acid sequence of the present invention as primers can be used.

The above discussion provides a factual basis for the use of genes to regulate hypoxia and ischemia and thereby also apoptosis and angiogenesis. The methods used with and the utility of the present invention can be shown by the following non-limiting example and accompanying figures.

EXAMPLE

Methods

Most of the techniques used in molecular biology are widely practiced in the art, and most practitioners are familiar with the standard resource materials which describe specific conditions and procedures. However, for convenience, the following paragraphs may serve as a guideline.

General methods in molecular biology: Standard molecular biology techniques known in the art and not specifically described were generally followed as in Sambrook et al., *Molecular Cloning: A Laboratory Manual*, Cold Springs Harbor Laboratory, New York (1989), and in Ausubel et al., *Current Protocols in Molecular Biology*, John Wiley and Sons, Baltimore, Md. (1989) particularly for the Northern Analysis and In Situ analysis and in Perbal, *A Practical Guide to Molecular Cloning*, John Wiley & Sons, New York (1988), and in Watson et al., *Recombinant DNA*, Scientific American Books, New York. Polymerase chain reaction (PCR) was carried out generally as in *PCR Protocols: A Guide To Methods And Applications*, Academic Press, San Diego, Calif. (1990).

Reactions and manipulations involving other nucleic acid techniques, unless stated otherwise, were performed as generally described in Sambrook et al., 1989, *Molecular Cloning: A Laboratory Manual*, Cold Spring Harbor Laboratory Press, and methodology as set forth in U.S. Pat. Nos. 4,666,828; 4,683,202; 4,801,531; 5,192,659 and 5,272,057 and incorporated herein by reference.

Additionally, In situ (In cell) PCR in combination with flow cytometry can be used for detection of cells containing specific DNA and mRNA sequences (Testoni et al, 1996, Blood 87:3822).

General methods in immunology: Standard methods in immunology known in the art and not specifically described are generally followed as in Stites et al. (eds), Basic and Clinical Immunology (8th Edition), Appleton & Lange, Norwalk, Conn. (1994) and Mishell and Shiigi (eds), Selected Methods in Cellular Immunology, W. H. Freeman and Co., New York (1980). Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, *Molecular Cloning: A Laboratory Manual*, Cold Springs Harbor, New York, 1989.

Differential Analysis

For example C6 glioma cells or other appropriate cells, cell lines or tissues are grown under normal conditions (Normoxia) or under oxygen deprivation conditions (Hypoxia) generally for four to sixteen hours. The cells are harvested and RNA is prepared from the cytoplasmic extracts and from the nuclear fractions. Following the extraction of RNA, fluorescent cDNA probes are prepared. Each condition (for example 4 hours hypoxia and normoxia) is labeled with a different fluorescent dye. For example a probe can be composed of a mixture of Cy3-dCTP cDNA prepared from RNA extracted from hypoxic cells and with Cy5-dCTP cDNA prepared from RNA extracted from normoxic cells. The probes are used for hybridization to microarray containing individually spotted cDNA clones derived from C6 cells that were exposed to hypoxia. Differential expression in measured by the amount of fluorescent cDNA that hybridizes to each of the clones on the array. Genes that are up regulated under hypoxia will have more fluorescence of Cy3 than Cy5. The results show genes that are transcriptionally induced mRNA species that respond very fast to hypoxia.

Differential Display

Reverse transcription: 2 μg of RTA are annealed with 1 pmol of oligo dT primer $(dT)_{18}$ in a volume of 6.5 μl by heating to 70° C. for five minutes and cooling on ice. 2 μl reaction buffer (×5), 1 μl of 10 mM dNTP mix, and 0.5 μl of Superscript II reverse transcriptase (GibcoBRL) is added. The reaction is carried for one hour at 42° C. The reaction is stopped by adding 70 μl TE (10 mM Tris pH=8; 1.01 mM EDTA).

Oligonucleotides used for Differential display: The oligonucleotides are generally those described in the Delta RNA Fingerprinting kit (Clonetech Labs. Inc.).

Amplification reactions: Each reaction is done in 20 μl and contains 50 μM dNTP mix, 1μM from each primer, 1× polymerase buffer, 1 unit expand Polymerase (Boehringer Mannheim), 2 μCi [α-$^{32}$P] dATP and 1 μl cDNA template. Cycling conditions are generally: three minutes at 95° C., then three cycles of two minutes at 94° C., five minutes at 40° C., five minutes at 68° C. This is followed by 27 cycles of one minute at 94° C., two minutes at 60° C., two minutes at 68° C. Reactions were terminated by a seven minute incubation at 68° C. and addition of 20 μl sequencing stop solution (95% formamide, 10 mM NaOH, 0.025% bromophenol blue, 0.025% xylene cyanol).

Gel analysis: Generally 3–4 μl are loaded onto a 5% sequencing polyacrylamide gel and samples are electrophoresed at 2000 volts/40 milliamperes until the slow dye (xylene cyanol) is about 2 cm from the bottom. The gel is transferred to a filter paper, dried under vacuum and exposed to x-ray film.

Recovery of differential bands: Bands showing any a differential between the various pools are excised out of the dried gel and placed in a microcentrifuge tube. 50 μl of sterile $H_2O$ are added and the tubes heated to 100° C. for five minutes. 1 μl is added to a 49 μl PCR reaction using the same primers used for the differential display and the samples are amplified for 30 cycles of: one minute at 94° C., one minute at 60° C. and one minute at 68° C. 10 μl is analyzed on agarose gel to visualize and confirm successful amplification.

Representational Difference Analysis

Reverse transcription: as above but with 2 μg polyA+ selected mRNA.

Preparation of double stranded cDNA: cDNA from the previous step is treated with alkali to remove the mRNA, precipitated and dissolved in 20 μl $H_2O$. 5 μl buffer, 2 μl 10 mM dATP, $H_2O$ to 48 μl and 2 μl terminal deoxynucleotide transferase (TdT) are added. The reaction is incubated 2–4 hours at 37° C. 5 μl oligo dT (1 μg/μl) was added and incubated at 60° C. for five minutes. 5 μl 200 mM DTT, 10 μl 10×section buffer (100 mM Mg $Cl_2$, 900 mM Hepes, pH 6.6) 16 μl dNSTPs (1 mM), and 16 U of Klenow are added and the mixture incubated overnight at room temperature to generate ds cDNA. 100 μl TE is added and extracted with phenol/chloroform. The DNA is precipitated and dissolved in 50 μl $H_2O$.

Generation of representations: cDNA with DpnII is digested by adding 3 μl DpnII reaction buffer 20 V and DpnII to 25 μl cDNA and incubated five hours at 37° C. 50 μl TE is added and extracted with phenol/chloroform. cDNA is precipitated and dissolved to a concentration of 10 ng/μl.

Driver: 1.2 μg DpnII digested cDNA. 4 μl from each oligo and 5 μl ligation buffer ×10 and annealed at 60° C. for ten minutes. 2 μl ligase is added and incubated overnight at 16° C. The ligation mixture is diluted by adding 140 μl TE. Amplification is carried out in a volume of 200 μl using appropriate primer and 2 μl ligation product and repeated in twenty tubes for each sample. Before adding Taq DNA polymerase, the tubes are heated to 72° C. for three minutes. PCR conditions are as follows: five minutes at 72° C., twenty cycles of one minute at 95° C. and three minutes at 72° C., followed by ten minutes at 72° C. Every four reactions were combined, extracted with phenol/chloroform and precipitated. Amplified DNA is dissolved to a concentration of 0.5 μg/μl and all samples are pooled.

Subtraction: Tester DNA (20 μg) is digested with DpnII as above and separated on a 1.2% agarose gel. The DNA is extracted from the gel and 2 μg ligated to the appropriate oligos. The ligated Tester DNA is then diluted to 10 ng/μl with TE. Driver DNA is digested with DpnII and repurified to a final concentration of 0.5 μg/μl. Mix 40 μg of Driver DNA with 0.4 μg of Tester DNA. Extraction is carried out with phenol/chloroform and precipitated using two washes with 70% ethanol, resuspended DNA in 4 μl of 30 mM EPPS pH=8.0, 3 mM EDTA and overlaid with 35 μl mineral oil. Denature at 98° C. for five minutes, cool to 67° C. and 1 μl of 5M NaCl added to the DNA. Incubate at 67° C. for twenty hours. Dilute DNA by adding 400 μl TE.

Amplification: Amplification of subtracted DNA in a final volume of 200 μl as follows: Buffer, nucleotides and 20 μl of the diluted DNA are added, heated to 72° C., and Taq DNA polymerase added. Incubate at 72° C. for five minutes and add appropriate oligo. Ten cycles of one minute at 95° C., three minutes at 70° C. are performed. Incubate ten minutes at 72° C. The amplification is repeated in four separate tubes. The amplified DNA is extracted with phenol/chloroform, precipitated and all four tubes combined in 40 μl 0.2×TE, and digested with Mung Bean Nuclease as follows: To 20 μl DNA 4 μl buffer, 14 μl $H_2O$ and 2 μl Mung Bean Nuclease (10 units/μl) added. Incubate at 30° C. for thirty-five minutes+First Differential Product (DPI).

Repeat subtraction hybridization and PCR amplification at driver: differential ratio of 1:400 (DPII) and 1:40,000 (DPIII) using appropriate oligonucleotides. Differential products are then cloned into a Bluescript vector at the BAM HI site for analysis of the individual clones.

Differential Expression Using Gene Expression Micro-array

Messenger RNA isolated as described herein above is labeled with fluorescent dNTP's using a reverse transcription reaction to generate a labeled cDNA probe. mRNA is extracted from C6 cells cultured in normoxia conditions and labeled with Cy3-dCTP (Amersham) and mRNA extracted from C6 cells cultured under hypoxia conditions is labeled with Cy5-dCTP (Amersham). The two labeled cDNA probes are then mixed and hybridized onto a microarray (Schena et al, 1996) composed of for example 2000 cDNA clones derived from a cDNA library prepared from C6 cells cultured under hypoxic conditions. Following hybridization the microarray is scanned using a laser scanner and amount of fluorescence of each of the fluorescent dyes is measured for each cDNA clone on the micro-array giving an indication of the level of mRNA in each of the original mRNA populations being tested. Comparison of the fluorescence on each cDNA clone on the micro-array between the two different fluorescent dyes is a measure for the differential expression of the indicated genes between the two experimental conditions.

In Situ Analysis

In situ analysis is performed for the candidate genes identified by the differential response to exposure to hypoxia conditions as described above. The expression is studied in two experimental systems: solid tumors and hypoxic retina.

Solid tumors are formed by injections in mice of the original glioma cells used for the differential expression. The glioma cells form tumors which are then excised, slided and used to individually measure expression levels of the candidate gene. The solid tumor model (Benjamin et al, 1997) shows that the candidate gene's expression is activated in tumors around the hypoxic regions that are found in the center of the tumor and are therefore hypoxia-regulated in vivo. Up regulation indicates further that the up-regulated gene can promote angiogenesis that is required to sustain tumor growth.

The hypoxia retina model measures expression levels in an organ that is exposed to hypoxia (ischemia) and directly mimics retinopathy. Hypoxia in the retina is created by exposing new born rats to hyperoxia which diminishes blood vessels in the retinas (Alon et al., 1995). Upon transfer to normal oxygen levels, relative hypoxia is formed due to the lack of blood supply. The hypoxia retina is excised, sliced and used to monitor the expression of the candidate genes.

Results

Utilizing gene expression microarray analysis the genes set forth in SEQ ID Nos:1–6 were identified as being differentially expressed under hypoxia conditions.

As shown in the figures differential expression under hypoxia conditions was observed. Northern Analysis was performed with 32P-dCTP labeled probes derived from the candidate genes. Two micrograms of mRNA were fractionated on formaldehyde containing agarose gels, blotted onto a nitrocellulose membrane and hybridized to the labeled cDNA probes. To monitor the kinetics of expression as a result of hypoxia, mRNA was prepared from cells in normoxia, and 4 and 16 hours exposure to hypoxia conditions. The results of the analysis showed that all the genes (SEQ ID Nos:1–6) were induced by hypoxic conditions, confirming the results obtained by the gene expression microarray analysis.

In the in situ analysis using the solid tumor model SEQ ID Nos:1–6 were upregulated, that is expressed. In the retina model SEQ ID Nos:1, 2 and 6 were found to be upregulated in this model.

SEQ ID No:1 (RTP801) is the rat homolog of SEQ ID No:2 (RTP779). The protein sequences are SEQ ID No:9 and SEQ ID No:10 respectively. Neither of these genes have been reported in gene data bases and both are expressed under hypoxic stress and are up-regulated in both of the in situ analyses. The expression of this gene was observed in the ovary where active apoptosis was occurring. Its regulation is HIF-1 dependent (Carmeliet et al, 1998) indicating further that the gene is associated with hypoxia-induced apoptosis. Some homology was found between the 3'UTR of RTP801 and the 5'UTR of a transcription factor (rat) pet-1 (Carmeliet et al, 1998; Spence et al, 1998; Fyodorov et al, 1998).

SEQ ID No:3 (RTP241) is 1902 bp long, has not been reported in gene data bases and is expressed under hypoxic stress and up-regulated in both in situ analyses. The gene sequence has some homology with a yeast gene located upstream to the cox14 gene. The protein (SEQ ID No:7) coded by the sequence contains a signal peptide region and therefore is secreted.

SEQ ID No:4 (RTP220) is 4719 bp long, has not been reported in gene data bases and is expressed under hypoxic stress and up-regulated in the tumor in situ analysis. The gene sequence has some homology with annilin from Drosophila. The protein sequence is set forth in SEQ ID No:11.

SEQ ID No:5 (RTP953/359) is a partial gene sequence that has not been found in gene data bases and is expressed under hypoxic stress and up-regulated in both in situ analyses.

SEQ ID No:6 (RTP971) is expressed under hypoxic stress and up-regulated in the tumor in situ analysis. The original analysis used the rat sequence. SEQ ID No:6 is the human homolog and has greater than 90% homology with the rat sequence. Based on preliminary sequence analysis it appears to be the gene Neuroleukin or a member of that gene family. The gene has not been reported to be responsive to hypoxia conditions and is reported to be a new motility factor for astrocytes. The reported gene encodes a protein (SEQ ID No:8, human homolog) that is identified as a glycolytic enzyme phosphohexose isomerase and as a survival factor for neurons (Niinaka et al, 1998; Watanabe et al., 1996).

Astrocyte motility is an important factor in the formation of blood vessels (angiogenesis) in brain and retina. Astrocytes can be considered oxygen level sensors as they respond under hypoxic conditions by secretion of angiogenic factors like WEGF. In an experiment primary astrocyte cultures were established and grown in vitro without serum and the astrocytes were immobile. However when conditioned medium from retinal cultures cultured under hypoxic conditions was added to the astrocyte cultures motility was observed. If the neuroleukin inhibitor (Obese et al., 1990), D-erythrose 4-phosphate (at 1.25 mM) was added clear indications of inhibition of motility were observed in the astrocyte cultures indicating that the astrocyte motility (and stellation) was dependent on neuroleukin activity. Other results show that SEQ ID No:6 is also HIF-1 dependent indicating further that the gene is associated with hypoxia-induced angiogenesis and apoptosis.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Alon, et al. (1995). Vascular endothelial growth factor acts as a survival factor for newly formed retinal vessels and has implications for retinopathy of prematurity. Nat Med. 1(10):1024–1028.

Benjamin, et al. (1997). Conditional switching of vascular endothelial growth factor (VEGF) expression in tumors: induction of endothelial cell shedding and regression of hemangioblastoma-like vessels by VEGF withdrawal. Proc Natl Acad Sci USA. 94(16):8761–8766.

Bouck, et al. (1996). How tumors become angiogenic. Adv. Cancer Res. 69:135–174.

Bunn, et al. (1996). Oxygen sensing and molecular adaptation in hypoxia. Physiol Rev. 76:839–885.

Burke and Olson, 1991. "Preparation of Clone Libraries in Yeast Artificial-Chromosome Vectors" in *Methods in Enzymology*, Vol. 194, "Guide to Yeast Genetics and Molecular Biology", eds. C. Guthrie and G. Fink, Academic Press, Inc., Chap. 17, pp. 251–270.

Capecchi, 1989. "Altering the genome by homologous recombination" *Science* 244:1288–1292.

Carmeliet, et al. (1998). Role of HIF-1alpha in hypoxia-mediated apoptosis; cell proliferation and tumour angiogenesis. Nature. 394(6692):485–490.

Davies et al., 1992. "Targeted alterations in yeast artificial chromosomes for inter-species gene transfer", *Nucleic Acids Research*, 20(11):2693–2698.

Dickinson et al., 1993. "High frequency gene targeting using insertional vectors", *Human Molecular Genetics*, 2(8):1299–1302.

Duff and Lincoln, 1995. "Insertion of a pathogenic mutation into a yeast artificial chromosome containing the human APP gene and expression in ES cells", *Research Advances in Alzheimer's Disease and Related Disorders*.

Dor, et al. (1997). Ischemia-driven angiogenesis. Trends Cardiovasc. Med. 7:289–294.

Duke, et al. (1996). Cell Suicide in Health and Disease. Scientific American. 80–87.

Fyodorov, et al. (1998). Pet-1, a novel ETS domain factor that can activate neuronal nAchR gene transcription. J Neurobiol. 34(2):151–163.

Gallagher et al., (1997). Identification of p53 Genetic Suppressor Elements Which Confer Resistance to Cisplatin. Oncogene 14:18514 193.

Gordon, 1989. Transgenic Animals. Intl. Rev. Cytol. 115:171–229.

Hanahan, et al. (1996). Patterns and Emerging Mechanisms of Angiogenic Switch During Tumorigenesis. Cell. 86:353–364.

Herskowitz (1987). Functional Inactivation of Genes By Dominant Negative Mutations. Nature 329(6136):219–222.

Holzmayer et al., (1992). Isolation of Dominant Negative Mutants and Inhibitory Antisense RNA Sequences by Expression Selection of Random DNA Fragments. Nucleic Acids Res 20(4):711–717.

Huston et al, 1991 "Protein engineering of single-chain Fv analogs and fusion proteins" in Methods in Enzymology (J J Langone, ed.; Academic Press, New York, N.Y.) 203:46–88.

Huxley et al., 1991. "The human HPRT gene on a yeast artificial chromosome is functional when transferred to mouse cells by cell fusion", Genomics, 9:742–750.

Jakobovits et al., 1993. "Germ-line transmission and expression of a human-derived yeast artificial chromosome", Nature, 362:255–261.

Johnson and Bird, 1991 "Construction of single-chain Fvb derivatives of monoclonal antibodies and their production in Escherichia coli in Methods in Enzymology (J J Langone, ed.; Academic Press, New York, N.Y.) 203:88–99.

Lamb et al., 1993. "Introduction and expression of the 400 kilobase precursor amyloid protein gene in transgenic mice", Nature Genetics, 5:22–29.

Lavitrano et al, 1989. Cell 57:717–723

Lo, 1983. Mol. Cell. Biol. 3:1803–1814.

Mansour, 1990. Gene targeting in murine embryonic stem cells: Introduction of specific alterations into the mammalian genome. GATA 7(8):219–227.

Mernaugh and Mernaugh, 1995 "An overview of phage-displayed recombinant antibodies" in Molecular Methods In Plant Pathology (R P Singh an U S Singh, eds.; CRC Press Inc., Boca Raton, Fla.) pp. 359–365.

Niinaka, et al. (1998). Expression and secretion of neuroleukin/phosphohexose isomerase/maturation factor as autocrine motility factor by tumor cells. Cancer Res. 58(12):2667–2674.

Obeso, et al. (1990). A Hemangioendothelioma-Derived Cell Line: Its Use as a Model for the Study of Endothelial Cell Biology. Laboratory Investigation. 83:259–264.

Pearson and Choi, 1993. Expression of the human β-amyloid precursor protein gene from a Yeast artificial chromosome in transgenic mice. Proc. Natl. Acad. Sci. USA, 90:10578–82.

Rothstein, 1991. "Targeting, disruption, replacement, and allele rescue: integrative DNA transformation in yeast" in Methods in Enzymology, Vol. 194, "Guide to Yeast Genetics and Molecular Biology", eds. C. Guthrie and G. Fink, Academic Press, Inc., Chap. 19, pp. 281–301.

Schedl et al., 1993. "A yeast artificial chromosome covering the tyrosinase gene confers copy number-dependent expression in transgenic mice", Nature, 362:258–261.

Schena et al., (1996) Parallel Human Genome Analysis: Microarray-based Expression Monitoring of 1000 genes. PNAS (USA) 93(20):10614–10619.

Spence, et al. (1998). Glucose metabolism in human malignant gliomas measured quantitatively with PET, 1-[C-11] glucose and FDG: analysis of the FDG lumped constant. J Nucl Med. 39(3):440–448.

Strauss et al., 1993. "Germ line transmission of a yeast artificial chromosome spanning the murine $\alpha_1$ (I) collagen locus", Science, 259:1904–1907.

Thompson et al, 1989. Cell 56:313–321.

Van der Putten et al, 1985. PNAS USA 82:6148–6152.

Watanabe, et al. (1996). Tumor cell autocrine motility factor is the neuroleukin/phosphohexose isomerase polypeptide. Cancer Res. 56(13):2960–2963.

Agrawal, 1996. Antisense oligonucleotides: towards clinical trials, TIBTECH, 14:376.

Akhter et al, 1991. Interactions of antisense DNA oligonucleotide analogs with phospholipid membranes (liposomes). Nuc. Res. 19:5551–5559.

Blaesse, 1997. Gene Therapy for Cancer. Scientific American 276(6):111–115.

Calabretta, et al, 1996. Antisense strategies in the treatment of leukemias. Semin. Oncol. 23:78.

Crooke, 1995. Progress in antisense therapeutics, Hematol. Pathol. 2:59.

Eckstein 1985. Nucleoside Phosphorothioates. Ann. Rev. Biochem. 54:367–402.

Felgner, 1997. Nonviral Strategies for Gene Therapy. Scientific American. June, 1997, pgs 102–106.

Gewirtz, 1993. Oligodeoxynucleotide-based therapeutics for human leukemias, Stem Cells Dayt. 11:96.

Galileo et al., 1991. J. Cell. Biol., 112:1285.

Hanania, et al 1995. Recent advances in the application of gene therapy to human disease. Am. J. Med. 99:537.

Iyer et al. 1990. J. Org. Chem. 55:4693–4699.

Lefebvre-d'Hellencourt et al, 1995. Immunomodulation by cytokine antisense oligonucleotides. Eur. Cytokine Netw. 6:7.

Lev-Lehman et al., 1997. Antisense Oligomers in vitro and in vivo. In Antisense Therapeutics, A. Cohen and S. Smicek, eds (Plenum Press, New York).

Loke et al, 1989. Characterization of oligonucleotide transport into living cells. PNAS USA 86:3474.

Morrison, 1991. Suppression of basic fibroblast growth factor expression by antisense oligonucleotides inhibits the growth of transformed human astrocytes. J. Biol. Chem. 266:728.

Radhakrishnan et al., 1990. The automated synthesis of sulfur-containing oligodeoxyribonucleotides using 3H-1, 2-Benzodithiol-3-One 1,1 Dioxide as a sulfur-transfer reagent. J. Org. Chem. 55:4693–4699.

Rosolen et al., 1990. Cancer Res. 50:6316.

Scanlon et al., 1995. Oligonucleotides-mediated modulation of mammalian gene expression. FASEB J. 9:1288.

Shaw et al., 1991. Modified deoxyoligonucleotides stable to exonuclease degradation in serum. Nucleic Acids Res. 19:747–750.

Spitzer and Eckstein 1988. Inhibition of deoxynucleases by phosphorothioate groups in oligodeoxyribonucleotides. Nucleic Acids Res. 18:11691–11704.

Uhlmann and Peyman, 1990. Antisense Oligonucleotides: A New Therapeutic Principle. Chem Rev 90(4):543–584.

Wagner et al., 1996. Potent and selective inhibition of gene expression by an antisense heptanucleotide. Nature Biotechnology 14:840–844.

Wagner, 1994. Gene inhibition using antisense oligodeoxynucleotides. Nature 372:333.

Whitesell et al., 1991. Episome-generated N-myc antisense RNA restricts the differentiation potential of primitive neuroectodermal cell lines. Mol. Cell. Biol. 11:1360.

Yakubov et al, 1989. PNAS USA 86:6454.

Wright & Anazodo, 1995. Antisense Molecules and Their Potential For The Treatment Of Cancer and AIDS. Cancer J. 8:185–189.

Woolf et al., 1990. The stability, toxicity and effectiveness of unmodified and phosphorothioate antisense oligodeoxynucleotides in Xenopus oocytes and embryos. Nucleic Acids Res. 18:1763–1769.

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
    (A) LENGTH: 1754 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1:

```
CCCCCGGGGG AGGTGCGAGA GGGCTGGAAA GGACAGGTCC GGGCAGCGAT CGGGGGTTGG      60
CATCAGTTCG CTCACCCTTC GAGAGGCAGA TCGCTCTTGT CCGCAATCTT CGCTGACCG     120
GCTAGCTGCG GCTTCTGTGC TCCTTCGCCG AACCTCATCA ACCAGCGTCC TGGCGTCTG     180
CCTCGCCATG CCTAGCCTTT GGGATCGTTT CTCGTCCTCC TCTTCCTCTT CGTCCTCGT     240
CCGAACTCCG GCCGCTGATC GGCCGCCGCG CTCCGCCTGG GGGTCTGCGG CCAGAGAAG     300
GGGCCTTGAC CGCTGCGCGA GCCTGGAGAG CTCGGACTGC GAGTCCCTGG ACAGCAGCA     360
CAGTGGCTTT GGGCCGGAGG AAGACTCCTC ATACCTGGAT GGGGTGTCTC TGCCTGACT     420
TGAGCTGCTC AGTGACCCCG AGGATGAGCA CCTGTGTGCC AACCTGATGC AGCTGCTGC     480
GGAGAGCCTG TCCCAGGCGC GATTGGGCTC GCGGCGCCCT GCGCGCCTGC TGATGCCGA     540
CCAGCTGTTG AGCCAGGTGG GCAAGGAACT CCTGCGCCTG GCGTACAGCG AGCCGTGCG     600
CCTGCGGGGG GCACTGCTGG ACGTCTGTGT GGAGCAAGGC AAGAGCTGCC ATAGTGTGG     660
TCAGCTGGCT CTGGACCCCA GTCTAGTGCC CACCTTTCAG TTGACCCTGG TGCTGCGTC     720
GGACTCTCGC CTCTGGCCCA AGATCCAGGG CCTGTTGAGT TCTGCCAACT CTTCCTTGG     780
CCCTGGTTAC AGCCAGTCCC TGACGCTGAG CACCGGCTTC AGAGTCATCA AAAAGAAAC     840
CTACAGCTCC GAGCAGCTGC TCATTGAAGA GTGTTGAACT TCGTCCTGGA GGGGGGCCG     900
ACTGCCCCCC AAAGTGGAGA CAAGGAATTT CTGTGGTGGA GACCCGCAGG CAAGGACTG     960
AGGACTGTCC CCTGTGTTAG AAAACTGACA ATAGCCACCG GAGGGCGCA GGGCCAGG     1020
GGAGAAGGAA GTGTTGTCCA GGAAGTCTCT AGGTTGTGTG CAGGTGGCCC CCTGTTGG    1080
CACATGCCCC TCAGTACTGT AGCATGAAAC AAAGGCTTCG GAGCCACACA GGCTTCTG    1140
TGGATGTGTA TGTAGCATGT ATCTTATTAA TTTTTGTATT ACTGACAAGT TACAACAG    1200
GTTGTGGGCC AGAGTCAGAA GGGCAGCTGG TCTGCACTGG CCTCTGCCCG GGCTGTGT    1260
TGGGGGGAGG CGGGGGGAGG TCTCCGACAG TTTGTCGACA GATCTCATGG TCTGAAAG    1320
CCGAGCTTGT TCGTCGTTTG GTTTGTATCT TGTTTTGGGG GTGGGTGGG GGGATCGG     1380
CTTCACTACT GACCTGTTCG AGGCAGCTAT CTTACAGACT GCATGAATGT AAGAATAG    1440
AGGGGGTGGG TGTTAGGATC ATTTGGGATC TTCAACACTT GAAACAAAAT AACACCAG    1500
AGCTGCATCC CAGCCCATCC CGGTGCCGGT GTACTGGAGG AGTGAACTGT GAGGGGAT    1560
GGCTGAGGGG GGTGGGGGGC TGGAACCCTC TCCCCCAGAG GAGCGCCACC TGGGTCTT    1620
ATCTAGAACT GTTTACATGA AGATACTCAC GGTTCATGAA TACACTTGAT GTTCAAGT    1680
```

| | |
|---|---|
| TAAGACCTAT GCAATATTTT TACTTTTCTA ATAAACATGT TTGTTAAAAC AAAAAAAA | 1740 |
| AAAAAAAAAA AAAA | 1754 |

(2) INFORMATION FOR SEQ ID NO: 2:

(i) SEQUENCE CHARACTERISTICS:
        (A) LENGTH: 1782 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 2:

| | |
|---|---|
| TTTGGCCCTC GAGGCCAAGA ATTCGGCACG AGGGGGGGAG GTGCGAGCGT GGACCTGGGA | 60 |
| CGGGTCTGGG CGGCTCTCGG TGGTTGGCAC GGGTTCGCAC ACCCATTCAA GCGGCAGGA | 120 |
| GCACTTGTCT TAGCAGTTCT CGCTGACCGC GCTAGCTGCG GCTTCTACGC TCCGGCACT | 180 |
| TGAGTTCATC AGCAAACGCC CTGGCGTCTG TCCTCACCAT GCCTAGCCTT TGGGACCGC | 240 |
| TCTCGTCGTC GTCCACCTCC TCTTCGCCCT CGTCCTTGCC CCGAACTCCC ACCCCAGAT | 300 |
| GGCCGCCGCG CTCAGCCTGG GGGTCGGCGA CCCGGGAGGA GGGGTTTGAC CGCTCCACG | 360 |
| GCCTGGAGAG CTCGGACTGC GAGTCCCTGG ACAGCAGCAA CAGTGGCTTC GGGCCGGAG | 420 |
| AAGACACGGC TTACCTGGAT GGGGTGTCGT TGCCCGACTT CGAGCTGCTC AGTGACCCT | 480 |
| AGGATGAACA CTTGTGTGCC AACCTGATGC AGCTGCTGCA GGAGAGCCTG GCCCAGGCG | 540 |
| GGCTGGGCTC TCGACGCCCT GCGCGCCTGC TGATGCCTAG CCAGTTGGTA AGCCAGGTG | 600 |
| GCAAAGAACT ACTGCGCCTG GCCTACAGCG AGCCGTGCGG CCTGCGGGGG GCGCTGCTG | 660 |
| ACGTCTGCGT GGAGCAGGGC AAGAGCTGCC ACAGCGTGGG CCAGCTGGCA CTCGACCCC | 720 |
| GCCTGGTGCC CACCTTCCAG CTGACCCTCG TGCTGCGCCT GGACTCACGA CTCTGGCCC | 780 |
| AGATCCAGGG GCTGTTTAGC TCCGCCAACT CTCCCTTCCT CCCTGGCTTC AGCCAGTCC | 840 |
| TGACGCTGAG CACTGGCTTC CGAGTCATCA AGAAGAAGCT GTACAGCTCG GAACAGCTG | 900 |
| TCATTGAGGA GTGTTGAACT TCAACCTGAG GGGGCCGACA GTGCCCTCCA AGACAGAGA | 960 |
| GACTGAACTT TGGGGTGGA GACTAGAGGC AGGAGCTGAG GGACTGATTC CTGTGGTT | 1020 |
| AAAACTGAGG CAGCCACCTA AGGTGGAGGT GGGGGAATAG TGTTTCCCAG GAAGCTCA | 1080 |
| GAGTTGTGTG CGGGTGGCTG TGCATTGGGG ACACATACCC CTCAGTACTG TAGCATGA | 1140 |
| CAAAGGCTTA GGGGCCAACA AGGCTTCCAG CTGGATGTGT GTGTAGCATG TACCTTAT | 1200 |
| TTTTTGTTAC TGACAGTTAA CAGTGGTGTG ACATCCAGAG AGCAGCTGGG CTGCTCCC | 1260 |
| CCCAGCCCGG CCCAGGGTGA AGGAAGAGGC ACGTGCTCCT CAGAGCAGCC GGAGGGAG | 1320 |
| GGGAGGTCGG AGGTCGTGGA GGTGGTTTGT GTATCTTACT GGTCTGAAGG GACCAAGT | 1380 |
| GTTTGTTGTT TGTTTTGTAT CTTGTTTTTC TGATCGGAGC ATCACTACTG ACCTGTTG | 1440 |
| GGCAGCTATC TTCAGACGC ATGAATGTAA GAGTAGGAAG GGGTGGGTGT CAGGGATC | 1500 |
| TTGGGATCTT TGACACTTGA AAAATTACAC CTGGCAGCTG CGTTTAAGCC TTCCCCCA | 1560 |
| GTGTACTGCA GAGTTGAGCT GGCAGGGGAG GGGCTGAGAG GGTGGGGGCT GGAACCCC | 1620 |
| CCCGGGAGGA GTGCCATCTG GGTCTTCCAT CTAGAACTGT TTACATGAAG ATAAGATA | 1680 |
| CACTGTTCAT GAATACACTT GATGTTCAAG TATTAAGACC TATGCAATAT TTTTTACT | 1740 |

TCTAATAAAC ATGTTTGTTA AAACAAAAAA AAAAAAAAAA AA       1782

(2) INFORMATION FOR SEQ ID NO: 3:

(i) SEQUENCE CHARACTERISTICS:
        (A) LENGTH: 1900 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 3:

CCATCCCTCA TAGGACTAAT TATAGGGTTG GGGGGGCCGC CCCCCCAGGT TCGAGTGGCG       60

ATGGGCCGCG GCTGGGGCTT GCTCGTCGGA CTCTTGGGCG TCGTGTGGCT GCTGCGGTC       120

GGCCAGGGCG AGGAGCAGCA GCAGGAGACA GCGGCACAGC GGTGTTTCTG TCAGGTTAG       180

GGTTACCTGG ATGACTGTAC CTGTGATGTC GAGACCATCG ATAAGTTTAA TAACTACAG       240

CTTTTCCCAA GACTACAAAA GCTCCTTGAA AGTGACTACT TTAGATACTA CAAGGTAAA       300

TTGAGGAAGC CATGTCCTTT CTGGAATGAC ATCAACCAAT GTGGAAGAAG AGACTGTGC       360

GTCAAACCCT GCCATTCTGA TGAAGTCCCT GATGGAATTA AGTCTGCGAG CTACAAGTA       420

TCCAAGGAAG CCAACCTCCT TGAGGAGTGT GAGCAGGCTG AGCGGCTCGG AGCAGTGGA       480

GAATCTCTGA GTGAGGAGAC CCAGAAGGCT GTTCTTCAGT GGACGAAACA CGATGATTC       540

TCAGACAGCT TCTGTGAAGT TGATGACATA CAGTCCCCCG ATGCTGAGTA TGTGGATTT       600

CTCCTTAACC CTGAGCGCTA CACAGGCTAC AAGGGGCCGG ACGCTTGGAG GATATGGAG       660

GTCATCTATG AAGAAAACTG CTTTAAGCCA CAGACAATTC AAAGGCCTTT GGCTTCGGG       720

CAAGGAAAAC ATAAAGAGAA CACATTTTAC AGCTGGCTAG AAGGCCTCTG TGTAGAAAA       780

AGAGCATTCT ACAGGCTTAT ATCTGGCCTA CACGCAAGCA TCAATGTACA TTTGAGTGC       840

AGGTATCTTT TACAAGATAA TTGGCTGGAA AAGAAATGGG GTCATAATGT CACAGAGTT       900

CAGCAGCGCT TTGATGGGGT TTTGACAGAA GGAGAAGGCC CCAGGAGGCT GAAGAACCT       960

TACTTTCTTT ACCTGATAGA GTTAAGGGCT CTCTCTAAAG TGCTTCCGTT TTTCGAGC       1020

CCAGATTTTC AGCTCTTCAC TGGAAATAAA GTTCAGGATG TGGAAAACAA AGAGTTAC       1080

CTGGAGATTC TTCATGAAGT CAAGTCATTT CCTTTGCATT TTGATGAGAA TTCTTTTT       1140

GCGGGGATA AAAACGAAGC ACATAAGCTA AAGGAGGACT TCCGCCTACA CTTTAGAA       1200

ATCTCGAGGA TCATGGACTG CGTCGGCTGC TTCAAGTGCC GCCTGTGGGG CAAGCTTC       1260

ACTCAGGGTC TGGGCACTGC TCTGAAGATC TTGTTTTCTG AAAAACTGAT CGCAAATA       1320

CCCGAAAGCG GACCCAGTTA TGAATTCCAG CTAACCAGAC AAGAAATAGT GTCGTTGT       1380

AATGCATTCG GAAGGATTTC ACAAGTGTG AGAGAATTAG AGAACTTCAG ACACTTGT       1440

CAGAATGTTC ACTGAGGAGG GCGGCTGGAA CCTGCTTGTT TCTGCACAGG GGAGTCCA       1500

GGGCAGAATG TCTGAGCACG GTGATTGCAG TGACCGTCCT GAGCCAAACG TTCATATC       1560

GCTGCCTTTG TCAAAGGAGA GATACATTGT TTTAAGTAAA TGACATTTTT AAACATTG       1620

TTCATGTTTA ATATTATTGT GAATAAAAGT AGTATTTTGG TAATGTACAA ATTTTAAT       1680

TAAGCAAAAG TAAGGTCATT AAATTGCCCT ATGATGGGGT TGGGGATTTA GCTCAGTG       1740

AGAGCTCTTG CCTAGGAAGC GCAAGGCCCT GGGTTCGGTC CCCAGCTCCG AAAAAAAA       1800

| | | | | |
|---|---|---|---|---|
| ACCCCCCCCC | CAAAAAAAAT | TGCCCCCATA | AAAAGGGTAG | GTGAATCCTG | CCCCAGGC | 1860 |
| TCCACCTAAA | TTTTTTTTTG | AAAACTTTTT | TCCCCCAAGG | | | 1900 |

(2) INFORMATION FOR SEQ ID NO: 4:

(i) SEQUENCE CHARACTERISTICS:
        (A) LENGTH: 4121 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 4:

| | | | | | |
|---|---|---|---|---|---|
| RTTTTTTTTT | CCTTTNNAAA | NGGNNAAAGN | NTTCCCCCCN | CCTTCCTTCN | ANTTAAAAAT | 60 |
| TTGGNANCCC | AAAANGCTTN | GGGGGGCNNN | GGGNNCCCNT | NGGGGNTTGG | GGAGTTNCN | 120 |
| CNGGNGANNT | TTNCAAGNAA | NTTAAANATT | TTTTCACCCA | ATCNCCNTTT | TGGGGAAAA | 180 |
| CCTTGCCTTC | ACCTTTCCAA | AGCCAACCCG | TTTTCAAAGG | CTTCAGGTAC | CCCCAGTTG | 240 |
| GGAGAAGGGG | CCTTTCTGGC | CAACCCTTGC | TGGCAAACGA | TTTGGTTCCT | GGGAAGATG | 300 |
| TGTTAAGCTA | ATTCATTCTG | CCAAAGCCAA | AATAGTGTAA | CAAGAACAGC | CTGGTACCG | 360 |
| CTTGTTTATC | CCAAATCTTC | TTCTGCAAGT | GGACCATCTG | CTAGCATCAA | TAGTAGCAG | 420 |
| GTTTCAGCAG | GAAGCTACAT | GCTGTTCCCA | AAGGGATGGC | AATGCCTCTG | TCAAGGAAA | 480 |
| ACCCAACTTC | AAATGCTGCC | GATGGGCCTT | TGCTTAAAGC | CTCAGTGTCC | AGCCCTGTG | 540 |
| AAGCATCTTC | TTCCCCTGTG | AGATCCGCTC | CATTCATCAC | TAGAAACTGT | GAGGTGCAG | 600 |
| GTCCTGAGCT | ACTTCACAAA | ACTGTTAGTC | CTCTGAAAAC | AGAGGTGTTG | AAACCATGT | 660 |
| AGAAGCCAAC | TTTATCCCAG | GCACTTCAGC | CCAAAGAGGG | AGCTAACAAG | GAAGTTTGT | 720 |
| TACAGTCACA | GTCCAAGGAC | AAACTTGCAA | CACCAGGAGG | AAGAGGAATT | AAGCCTTTC | 780 |
| TGGAACGCTT | TGGAGAGCGT | TGTCAAGAAC | ACAGTAAAGA | AAGTCCAACT | TGCAGAGCA | 840 |
| TTCATAGAAC | CCCAAATATC | ACTCCAAATA | CAAAAGCTAT | CCAGGAAAGA | TTATTCAAG | 900 |
| AAAACACGTG | TTTCATCTAC | TACCCCAATT | TAGCACAGCA | GCTCAAACAG | GAGCGTGAA | 960 |
| AGGAACTGGC | GTGTCTCCGT | GGCCGATTTG | ACAAGGGCAG | TCTCTGGAGT | GCAGAGAA | 1020 |
| ATGAAAAGTC | AAGAAGCAAA | CAGCTAGAAA | CCAACAGGAA | GTTCACTGTC | AGAACTCT | 1080 |
| CCTCAAGAAA | CACCAAATTG | TCTCAAGGCA | CCCCGTCGAC | CTCTGTGTCA | GATAAAGT | 1140 |
| CTGAGACTCC | AACCGCAGTG | AAGATTTCTG | GTACAGAGCC | TGCAGGTTCC | ACTGAAAG | 1200 |
| AAATGACAAA | GTCCAGCCCT | TTGAAAATAA | CATTGTTTTT | AGAAGAGGAG | AAGTCCTT | 1260 |
| AAGTAGCATC | AGACCCGGAG | GTTGAGCAGA | AGACTGAAGC | AGTGCATGAA | GTAGAGAT | 1320 |
| GTGTGGACGA | TGAGGATATC | AACAGCTCCA | AGTCATTAAC | GACATCTTCA | GTGANTTC | 1380 |
| TAGNGGAANG | GGGAACTGGA | CNGTGGAAAA | GANCCAAGGA | GGAGATGGAC | CAAGTGGG | 1440 |
| ACGGAAAGCA | GCGAGGNGCA | GGAAGATGTG | CNGAATATCT | CCTCAATNTC | TTNACANG | 1500 |
| CCCGCTGGCT | CAGACGGTTC | GGCGTGGTGA | ATCTACAGAA | TGTAATTTCT | TCACCTGA | 1560 |
| TGGAATTGAG | AGACTATAGC | CTGAGTGCTC | CAAGTCCCAA | ACCAGGAAAA | TTCCAAAG | 1620 |
| CTCGTGTCCC | CCGAGCAGAA | TCTGGTGACA | GCCTCAGTTC | TGAGGACCGG | GACCTTCT | 1680 |
| ACAGCATTGA | TGCATATAGG | TCTCAAAGAT | TCAAAGAAAC | AGAACGCCCT | TCCATAAA | 1740 |

```
AAGTGATTGT TCGAAAGGAA GATGTTACTT CAAAATTGAG TGAAAAGAAT GGTGTCTT      1800

CTGGTCAAGT TAATATCAAA CAAAAAATGC AGGAACTCAA TAATGACATA AATTTGCA      1860

AGACAGTGAT CTATCAGGCC AGCCAGGCTC TCAACTGCTG TGTTGATGAA GAGCACGG      1920

AAGGATCCCT GGAAGAAGCT GAGGCAGAAA GGCTCTTTCT GANTGCAACT GAGAAAAG      1980

CACTTCTGAT TGACGAACTG AATAAGCTGA AGAGTGAAGG ACCTCAGAGG AGAAACAA      2040

CCGCTGTCGC ATCCCAGAGT GGATTTGCCC CATGTAAAGG GTCAGTCACC TTGTCAGA      2100

TCTGCCTGCC TCTGAAGGCA GAGTTTGTAT GCAGCACCGC GCAAAAGCCA GAGTCATC      2160

ATTACTACTA CTTAATTATG CTAAAAGCTG GGGCTGAGCA GATGGTGGCC ACCCCATT      2220

CAAGTACTGC AACTCTCTTA GTGGTGATGN CCCTGACATT CCCCACCACG TTACCCCN      2280

ANGATGTTTC CAATGACTTT GAAATAAATG TTGAAGTTTA CAGCTTGGTA CAAAAGAA      2340

ATTCCCTCAG GCCTGAGAAG AAGAAGAAGG CGTCCAAGTT TAAGGCTATT ACTCAAAA      2400

GACTCCTCAC ATCTATAACT TCAAAAAGCA GCCTTCATGC TTCAGTTATG CCAGTCC       2460

GAGGTCTCAG TGCTGTGCGC ACCAGCAACT TTACCCTAGT TGGATCTCAC ACACTCTC      2520

TATCTTCTGT TGGAGACACT AAGTTTGCTT TGGACAAGGT ACCTTTTTTG TCTCCGTT      2580

AAGGTCACAT CTGTTTAAAA ATAAGCTGTC AAGTGAATTC AGCTGTTGAG GAAAAGGG      2640

TCCTTACCAT ATTTGAAGAT GTTAGTGGCT TTGGTGCCTG GCACCGAAGA TGGTGTGT      2700

TCTCTGGCAA CTGTATCTCT TACTGGACTT ACCCAGATGA TGAGAGGCGA AGAATCC       2760

TAGGAAGGAT AAATCTGGCC AATTGTATCA GTCATCAGAT AGAACCAGCC AACAGAGA      2820

TTTGTGCAAG ACGCAACACT CTGGAATTGA TTACTGTCCG ACCACAAAGA GAAGACGA      2880

GAGAAACTCT TGTCAGCCAT GTAGAGACAC ACTCTGTGTC ACCCAAGAAC TGGCTCTC      2940

CAGATACTAA AGAAGAGCGG GATCTCTGGA TGCAGAAACT CAACCAGGTC ATTGTTGA      3000

TTCGCCTCTG GCAGCCTGAT GCATGCTACA AGCCTGTTGG GAAGCCTTAA GCCGAGGA      3060

TTCTGCACCG TGAGAGACTT TGCTAGCTGT GTCTTCTTAA GAAGACAGTT AGAAGCAG      3120

GATTTGCAGG TTGTATTCTA TGCTTTAAAT ATAAAAGGGT ATGTGCAAAT ATTCACTA      3180

TATTGTGCAG TATTTATATC TTTTCTATGT AAAACTTCAC CCAGTTTGTC TTGCATTC      3240

ACATGTTTGA CAGTCAAATA CTAACAATAT TCATGAGAAT TGATATCCAT GCTAAATA      3300

ACATTAAGAG TCTTGTTTTA TAGAAACCTC ACTAGCCAGT TATTCATGAC AAAAACTA      3360

ATAATCAAGT TCTGATTTGT CCTTTGGAGC TGTGGGTTTG AAGGTATTAA GGTCTCAA      3420

AGAAACATTT CAGGACATGT TTAGTAAAGA GATGAGAAAA GGCAGCAAAC ACTAGTTT      3480

GCTGCTCAGA GCTGCTTTCC GCAGAGCTGT GGGCAGGACA CCGTAACATT TGGGCCTG      3540

TAGTCTATGC TGAAGGGTTA AGAGTCACAC AGCTAGTGCT CACTCTGACC CTACGTGT      3600

AGTGTGGGGC ACCTTCTCAC AGTGCTCAGG CTTTACTTAA ACAGCTATTT TTCATGTA      3660

TGAGGATCCT CATTAACATG TTCAGCCTTT TCTCTTATAA CAAGAGCAAA TGTAAATT      3720

AAAAACACAT ACATAAGGAA TTTCTACCAA GCTGCTGTGA CTACTCCTTT GCTTCCCA      3780

GTTCTTGTCT CGTTTTCCTT TCATGTTGAT CTAAAACACT TTACAAATCT GTTTTGAG      3840

CACTGAAAAA TATATAAAGC TATGCATTCC CTTTAAAGCC CAATGCCTTC TTGCAATT      3900

AAAATATTAC AATGCATGGC TGCAGTTTTT AAATAGTCTG TGTTTCTCCT CTGACTGT      3960

GTTTATTGAT GGTTTCATTT ATAAAACACT AAATTCTATC ACTTGCCATT ATATTTCT      4020

CTCCATTTAA ATGTGGGTTT TCTTATGTAT ATTATAAAAG TATTTTATGA CTCCTACA      4080
```

| AATAAATAAT GTGGAATTGT CNAAANCAAA AAAAAAAAAA A | 4121 |

(2) INFORMATION FOR SEQ ID NO: 5:

(i) SEQUENCE CHARACTERISTICS:
        (A) LENGTH: 2059 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 5:

| ACAAACCACC AAACCACCAA ACCTGTTTAC TCAGATTCAT GGATTGTTCA CATATGTTTT | 60 |
| AACCACTCAC CCCACCTCAC AGAGGTGACC GAACCCAGGA CTTCAGTCAT GCTGGGCTA | 120 |
| CCCTGCATCC ATGAGCTGTG TGCCCTCAGG CCCTTGCTTA AGCTCCTACG TAGACGTAG | 180 |
| TGTCCTGTTT TTATTTAAGG ATTTGAAAAC CAGTCATGGG CACCATGATT TAACACAAA | 240 |
| TACTTCAGTG TGATGGTCTA ATTTCCTGAA ATAATTGTT TGTTCTTCTT TCAAGGAAA | 300 |
| ACCAAACCTT ATGAATCCGA GCCGAACTAT TATAAGCCTT AAAATAAGGA GCCGCCCGC | 360 |
| CCACATCCCA GTCACCCAGT GTTTGAGTTT GGTTGCCCTT TCTCACCTGT GTAATCACA | 420 |
| GGTATACAAT TCATGTTTCT TATGCATGAA ATTAATTTTC TTTCCCTCTG TGGAGTGGG | 480 |
| CTATATTTTA GACAGGTTTT TATTCGTGGA AGCTCTTCAC TGAGAGCAAT ATTTGAAGT | 540 |
| GCTTAAGAAT TTACGTCACA GCATTTATAA ATGATATACC TCAAAGTTAT GCTCCTTTG | 600 |
| TGTCATATAA TGTCTTGAGC AGTTAGGACA GGTTGAGATG TGACATAAGA AAAAGCAGG | 660 |
| TATGTATGTA ATGGATAGGA ATGTCACTTT ACACTGTTGT GTATTTCTC TGTCCCTAA | 720 |
| ACTTGGTGTA GTGCCAAGCA TACAGTTGGT ATCTAATTTT TGTTGATGGA AAGTGTATG | 780 |
| ATTTAGTATA CCTTAAGTGA ATGGTGTAGC TTGTGTAACA ATGTACCCTA TCTCCCCTT | 840 |
| CCTCTCACTT TTTCTTTCAA ATCGCATAAT AAACCCACAG ATTAGATCAG CTTTCTGGG | 900 |
| GGCGACTTCG AAAAGTACTA AATGATCACC GCACAGAAGC CAGCCCTTTG AAACCCTCA | 960 |
| TGCTTTCACT TGCGTTCTCC CACTTGACTG TCCCTGTGTC CTCTGTCTCT CCAAGGAA | 1020 |
| TCTAAACTCC TACGTCTTTC GTTAACAAGC AGTTTAATTT TTAAGAAATC TTAACTTT | 1080 |
| CTGTGCTTGA CACAATTGAC AATCCCTTTC TTCAAGCCCC ACCACTCTGC GTCCTTGT | 1140 |
| CTGGCTTGCT CCTGGGTCTC TTCCTTCTGG TCTCTTCATG TAACCGAAAT ATTAATTC | 1200 |
| CAGACTTTTC TTTCTTGCTC TAAGTCACTG GACCATACTC TTGTGTAATT TCCATGCA | 1260 |
| CATCTTATCT TAGCTTCTGT TTTCCTGCTG CGGTCACTTG GCTACCTGTT GCCACGTC | 1320 |
| CAAGGACTCA CTTCGTTTGC GCTCCTCACT TGGTTAGTTT CAGAACATTA CACTGTTC | 1380 |
| GGTTCTCCAG TTCGCTCTTC TGTCTTCTGC CTGACTATCG GTGTCTACGT TCTGCTGC | 1440 |
| CTACTCCAAC ATTTCTATCA CTGTCTTTCA ATTTTTATTA CAGTTACTCA AAGGATTT | 1500 |
| TGTGTTTATT TTCCCATCTC TGTTGGCCCA GATTACCGAA TTGGGCTTTC TAGAAGCA | 1560 |
| CAGCCTCATC CCTGCTACAG GCAGTTTTAG GAGCTTTTTG GTGAGAGTCT CTGCTTGG | 1620 |
| TCTAAGACCC TCCTCTTGTG TTTGCCACTC TGCTCTGATA AGAGTGTTAA AGAGTTTT | 1680 |
| AGAAGTCCAG AGTTGTAGCC CTCCAGACCT TCGTAGACAC CATATTTGCA TGGAGAGC | 1740 |
| TAGGCTTCTT CTGGGAAACT CCATGCGTTC TTGAGACTCT GTGACATTAA TTACCCTG | 1800 |

```
CCTTCCTTTG GTCACCATTA TAGTTGCAAC CTACCTCTAT TGAATCACTT ATTGTACT        1860

ATATTTTATT TTTTAAAGTG TCCTTTACTA GAATGTGAGC TCCTCAGGGG CAGGCAAA        1920

AACTTCATTC ATTTGGCATC TCTATAGCAT AATGTTTGGT ATATGAGCAT TTAATAAA        1980

TTGAATAAAT TGCTTCACAT GACAGCTGTT CCTCATGGCG GGCGTCTTCA CTGCCTTT        2040

TGCAAAACGG GGGGGAAAA                                                   2059

(2) INFORMATION FOR SEQ ID NO: 6:

(i) SEQUENCE CHARACTERISTICS:
        (A) LENGTH: 1987 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 6:

CTCGAGAGCT CCGCCATGGC CGCTCTCACC CGGGACCCCC AGTTCCAGAA GCTGCAGCAA        60

TGGTACCGCG AGCACCGCTC CGAGCTGAAC CTGCGCCGCC TCTTCGATGC CAACAAGGA        120

CGCTTCAACC ACTTCAGCTT GACCCTCAAC ACCAACCATG GGCATATCCT GGTGGATTA        180

TCCAAGAACC TGGTGACGGA GGACGTGATG CGGATGCTGG TGGACTTGGC CAAGTCCAG        240

GGCGTGGAGG CCGCCCGGGA GCGGATGTTC AATGGTGAGA AGATCAACTA CACCGAGGG        300

CGAGCCGTGC TGCACGTGGC TCTGCGGAAC CGGTCAAACA CACCCATCCT GGTAGACGG        360

AAGGATGTGA TGCCAGAGGT CAACAAGGTT CTGGACAAGA TGAAGTCTTT CTGCCAGCG        420

GTCCGGAGCG GTGACTGGAA GGGGTACACA GGCAAGACCA TCACGGACGT CATCAACAT        480

GGCATTGTCG GCTCCGACCT GGGACCCCTC ATGGTGACTG AAGCCCTTAA GCCATACTC        540

TCAGGAGGTC CCCGCGTCTG GTATGTCTCC AACATTGATG GAACTCACAT TGCCAAAAC        600

CTGGCCCAGC TGAACCCGGA GTCCTCCCTG TTCATCATTG CCTCCAAGAC CTTTACTAC        660

CAGGAGACCA TCACGAATGC AGAGACGGCG AAGGAGTGGT TTCTCCAGGC GGCCAAGGA        720

CCTTCTGCAG TGGCGAAGCA CTTTGTTGCC CTGTCTACTA ACACAACCAA AGTGAAGGA        780

TTTGGAATTG ACCCTCAAAA CATGTTCGAG TTCTGGGATT GGGTGGGAGG ACGCTACTC        840

CTGTGGTCGG CCATCGGACT CTCCATTGCC CTGCACGTGG GTTTTGACAA CTTCGAGCA        900

CTGCTCTCGG GGGCTCACTG GATGGACCAG CACTTCCGCA CGACGCCCCT GGAGAAGAA        960

GCCCCCGTCT TGCTGGCCCT GCTGGGTATC TGGTACATCA ACTGCTTTGG GTGTGAGA        1020

CACGCCATGC TGCCCTATGA CCAGTACCTG CACCGCTTTG CTGCGTACTT CCAGCAGG        1080

GACATGGAGT CCAATGGGAA ATACATCACC AAATCTGGAA CCCGTGTGGA CCACCAGA        1140

GGCCCCATTG TGTGGGGGGA GCCAGGGACC AATGGCCAGC ATGCTTTTTA CCAGCTCA        1200

CACCAAGGCA CCAAGATGAT ACCCTGTGAC TTCCTCATCC CGGTCCAGAC CCAGCACC        1260

ATACGGAAGG GTCTGCATCA CAAGATCCTC CTGGCCAACT TCTTGGCCCA GACAGAGG        1320

CTGATGAGGG GAAAATCGAC GGAGGAGGCC CGAAAGGAGC TCCAGGCTGC GGGCAAGA        1380

CCAGAGGACC TTGAGAGGCT GCTGCCACAT AAGGTCTTTG AAGGAAATCG CCCAACCA        1440

TCTATTGTGT TCACCAAGCT CACACCATTC ATGCTTGGAG CCTTGGTCGC CATGTATG        1500

CACAAGATCT TCGTTCAGGG CATCATCTGG GACATCAACA GCTTTGACCA GTGGGGAG        1560
```

```
GAGCTGGGAA AGCAGCTGGC TAAGAAAATA GAGCCTGAGC TTGATGGCAG TGCTCAAG      1620

ACCTCTCACG ACGCTTCTAC CAATGGGCTC ATCAACTTCA TCAAGCAGCA GCGCGAGG      1680

AGAGTCCAAT AAACTCGTGC TCATCTGCAG CCTCCTCTGT GACTCCCCTT TCTCTTCT      1740

TCCCTCCTCC CCGGAGCCGG CACTGCATGT TCCTGGACAC CACCCAGAGC ACCCTCTG      1800

TGTGGGCTTG GACCACGAGC CCTTAGCAGG GAAGGCTGGT CTCCCCCAGC CTAACCCC      1860

GCCCCTCCAT GTCTATGCTC CCTCTGTGTT AGAATTGGCT GAAGTGTTTT TGTGCAGC      1920

ACTTTTCTGA CCCATGTTCA CGTTGTTCAC ATCCCATGTA GAAAAACAAA GATGCCAC      1980

AGGAGGT                                                               1987

(2) INFORMATION FOR SEQ ID NO: 7:

(i) SEQUENCE CHARACTERISTICS:
        (A) LENGTH: 464 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO: 7:

Met Gly Arg Gly Trp Gly Leu Leu Val Gly Leu Leu Gly Val Val Tr
1               5                   10                  15

Leu Leu Arg Ser Gly Gln Gly Glu Glu Gln Gln Gln Glu Thr Ala Al
            20                  25                  30

Gln Arg Cys Phe Cys Gln Val Ser Gly Tyr Leu Asp Asp Cys Thr Cy
        35                  40                  45

Asp Val Glu Thr Ile Asp Lys Phe Asn Asn Tyr Arg Leu Phe Pro Ar
    50                  55                  60

Leu Gln Lys Leu Leu Glu Ser Asp Tyr Phe Arg Tyr Tyr Lys Val As
65                  70                  75                  80

Leu Arg Lys Pro Cys Pro Phe Trp Asn Asp Ile Asn Gln Cys Gly Ar
                85                  90                  95

Arg Asp Cys Ala Val Lys Pro Cys His Ser Asp Glu Val Pro Asp Gl
            100                 105                 110

Ile Lys Ser Ala Ser Tyr Lys Tyr Ser Lys Glu Ala Asn Leu Leu Gl
        115                 120                 125

Glu Cys Glu Pro Ala Glu Arg Leu Gly Ala Val Asp Glu Ser Leu Se
    130                 135                 140

Glu Glu Thr Gln Lys Ala Val Leu Gln Trp Thr Lys His Asp Asp Se
145                 150                 155                 160

Ser Asp Ser Phe Cys Glu Val Asp Asp Ile Gln Ser Pro Asp Ala Gl
                165                 170                 175

Tyr Val Asp Leu Leu Leu Asn Pro Glu Arg Tyr Thr Gly Tyr Lys Gl
            180                 185                 190

Pro Asp Ala Trp Arg Ile Trp Ser Val Ile Tyr Glu Glu Asn Cys Ph
        195                 200                 205

Lys Pro Gln Thr Phe Gln Arg Pro Leu Ala Ser Gly Gln Gly Lys Hi
    210                 215                 220

Lys Glu Asn Thr Phe Tyr Ser Trp Leu Glu Gly Leu Cys Val Glu Ly
225                 230                 235                 240

Arg Ala Phe Tyr Arg Leu Ile Ser Gly Leu His Ala Ser Ile Asn Va
                245                 250                 255
```

```
His Leu Ser Ala Arg Tyr Leu Leu Gln Asp Asn Trp Leu Glu Lys Ly
                260                 265                 270

Trp Gly His Asn Val Thr Glu Phe Gln Gln Arg Phe Asp Gly Val Le
            275                 280                 285

Thr Glu Gly Glu Gly Pro Arg Arg Leu Lys Asn Leu Tyr Phe Leu Ty
    290                 295                 300

Leu Ile Glu Leu Arg Ala Leu Ser Lys Val Leu Pro Phe Phe Glu Ar
305                 310                 315                 320

Pro Asp Phe Gln Leu Phe Thr Gly Asn Lys Val Gln Asp Val Glu As
                325                 330                 335

Lys Glu Leu Leu Leu Glu Ile Leu His Glu Val Lys Ser Phe Pro Le
                340                 345                 350

His Phe Asp Glu Asn Ser Phe Ala Gly Asp Lys Asn Glu Ala Hi
                355                 360                 365

Lys Leu Lys Glu Asp Phe Arg Leu His Phe Arg Asn Ile Ser Arg Il
        370                 375                 380

Met Asp Cys Val Gly Cys Phe Lys Cys Arg Leu Trp Gly Lys Leu Gl
385                 390                 395                 400

Thr Gln Gly Leu Gly Thr Ala Leu Lys Ile Leu Phe Ser Glu Lys Le
                405                 410                 415

Ile Ala Asn Met Pro Glu Ser Gly Pro Ser Tyr Glu Phe Gln Leu Th
                420                 425                 430

Arg Gln Glu Ile Val Ser Leu Phe Asn Ala Phe Gly Arg Ile Ser Th
                435                 440                 445

Ser Val Arg Glu Leu Glu Asn Phe Arg His Leu Leu Gln Asn Val Hi
        450                 455                 460

(2) INFORMATION FOR SEQ ID NO: 8:

(i) SEQUENCE CHARACTERISTICS:
        (A) LENGTH: 558 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO: 8:

Met Ala Ala Leu Thr Arg Asp Pro Gln Phe Gln Lys Leu Gln Gln Tr
1               5                   10                  15

Tyr Arg Glu His Arg Ser Glu Leu Asn Leu Arg Arg Leu Phe Asp Al
            20                  25                  30

Asn Lys Asp Arg Phe Asn His Phe Ser Leu Thr Leu Asn Thr Asn Hi
        35                  40                  45

Gly His Ile Leu Val Asp Tyr Ser Lys Asn Leu Val Thr Glu Asp Va
    50                  55                  60

Met Arg Met Leu Val Asp Leu Ala Lys Ser Arg Gly Val Glu Ala Al
65                  70                  75                  80

Arg Glu Arg Met Phe Asn Gly Glu Lys Ile Asn Tyr Thr Glu Gly Ar
                85                  90                  95

Ala Val Leu His Val Ala Leu Arg Asn Arg Ser Asn Thr Pro Ile Le
            100                 105                 110

Val Asp Gly Lys Asp Val Met Pro Glu Val Asn Lys Val Leu Asp Ly
        115                 120                 125

Met Lys Ser Phe Cys Gln Arg Val Arg Ser Gly Asp Trp Lys Gly Ty
```

```
          130                 135                 140
Thr Gly Lys Thr Ile Thr Asp Val Ile Asn Ile Gly Ile Val Gly Se
145                 150                 155                 160

Asp Leu Gly Pro Leu Met Val Thr Glu Ala Leu Lys Pro Tyr Ser Se
                165                 170                 175

Gly Gly Pro Arg Val Trp Tyr Val Ser Asn Ile Asp Gly Thr His Il
                180                 185                 190

Ala Lys Thr Leu Ala Gln Leu Asn Pro Glu Ser Ser Leu Phe Ile Il
                195                 200                 205

Ala Ser Lys Thr Phe Thr Thr Gln Glu Thr Ile Thr Asn Ala Glu Th
                210                 215                 220

Ala Lys Glu Trp Phe Leu Gln Ala Ala Lys Asp Pro Ser Ala Val Al
225                 230                 235                 240

Lys His Phe Val Ala Leu Ser Thr Asn Thr Thr Lys Val Lys Glu Ph
                245                 250                 255

Gly Ile Asp Pro Gln Asn Met Phe Glu Phe Trp Asp Trp Val Gly Gl
                260                 265                 270

Arg Tyr Ser Leu Trp Ser Ala Ile Gly Leu Ser Ile Ala Leu His Va
                275                 280                 285

Gly Phe Asp Asn Phe Glu Gln Leu Leu Ser Gly Ala His Trp Met As
                290                 295                 300

Gln His Phe Arg Thr Thr Pro Leu Glu Lys Asn Ala Pro Val Leu Le
305                 310                 315                 320

Ala Leu Leu Gly Ile Trp Tyr Ile Asn Cys Phe Gly Cys Glu Thr Hi
                325                 330                 335

Ala Met Leu Pro Tyr Asp Gln Tyr Leu His Arg Phe Ala Ala Tyr Ph
                340                 345                 350

Gln Gln Gly Asp Met Glu Ser Asn Gly Lys Tyr Ile Thr Lys Ser Gl
                355                 360                 365

Thr Arg Val Asp His Gln Thr Gly Pro Ile Val Trp Gly Glu Pro Gl
                370                 375                 380

Thr Asn Gly Gln His Ala Phe Tyr Gln Leu Ile His Gln Gly Thr Ly
385                 390                 395                 400

Met Ile Pro Cys Asp Phe Leu Ile Pro Val Gln Thr Gln His Pro Il
                405                 410                 415

Arg Lys Gly Leu His His Lys Ile Leu Leu Ala Asn Phe Leu Ala Gl
                420                 425                 430

Thr Glu Ala Leu Met Arg Gly Lys Ser Thr Glu Glu Ala Arg Lys Gl
                435                 440                 445

Leu Gln Ala Ala Gly Lys Ser Pro Glu Asp Leu Glu Arg Leu Leu Pr
                450                 455                 460

His Lys Val Phe Glu Gly Asn Arg Pro Thr Asn Ser Ile Val Phe Th
465                 470                 475                 480

Lys Leu Thr Pro Phe Met Leu Gly Ala Leu Val Ala Met Tyr Glu Hi
                485                 490                 495

Lys Ile Phe Val Gln Gly Ile Ile Trp Asp Ile Asn Ser Phe Asp Gl
                500                 505                 510

Trp Gly Val Glu Leu Gly Lys Gln Leu Ala Lys Lys Ile Glu Pro Gl
                515                 520                 525

Leu Asp Gly Ser Ala Gln Val Thr Ser His Asp Ala Ser Thr Asn Gl
                530                 535                 540

Leu Ile Asn Phe Ile Lys Gln Gln Arg Glu Ala Arg Val Gln
545                 550                 555
```

(2) INFORMATION FOR SEQ ID NO: 9:

(i) SEQUENCE CHARACTERISTICS:
        (A) LENGTH: 229 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO: 9:

```
Met Pro Ser Leu Trp Asp Arg Phe Ser Ser Ser Ser Ser Se
1               5                   10                  15

Ser Ser Arg Thr Pro Ala Ala Asp Arg Pro Pro Arg Ser Ala Trp Gl
                20                  25                  30

Ser Ala Ala Arg Glu Glu Gly Leu Asp Arg Cys Ala Ser Leu Glu Se
            35                  40                  45

Ser Asp Cys Glu Ser Leu Asp Ser Ser Asn Ser Gly Phe Gly Pro Gl
        50                  55                  60

Glu Asp Ser Ser Tyr Leu Asp Gly Val Ser Leu Pro Asp Phe Glu Le
65                  70                  75                  80

Leu Ser Asp Pro Glu Asp Glu His Leu Cys Ala Asn Leu Met Gln Le
                85                  90                  95

Leu Gln Glu Ser Leu Ser Gln Ala Arg Leu Gly Ser Arg Arg Pro Al
                100                 105                 110

Arg Leu Leu Met Pro Ser Gln Leu Leu Ser Gln Val Gly Lys Glu Le
            115                 120                 125

Leu Arg Leu Ala Tyr Ser Glu Pro Cys Gly Leu Arg Gly Ala Leu Le
        130                 135                 140

Asp Val Cys Val Glu Gln Gly Lys Ser Cys His Ser Val Ala Gln Le
145                 150                 155                 160

Ala Leu Asp Pro Ser Leu Val Pro Thr Phe Gln Leu Thr Leu Val Le
                165                 170                 175

Arg Leu Asp Ser Arg Leu Trp Pro Lys Ile Gln Gly Leu Leu Ser Se
            180                 185                 190

Ala Asn Ser Ser Leu Val Pro Gly Tyr Ser Gln Ser Leu Thr Leu Se
        195                 200                 205

Thr Gly Phe Arg Val Ile Lys Lys Leu Tyr Ser Ser Glu Gln Le
    210                 215                 220

Leu Ile Glu Glu Cys
225
```

(2) INFORMATION FOR SEQ ID NO: 10:

(i) SEQUENCE CHARACTERISTICS:
        (A) LENGTH: 232 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO: 10:

```
Met Pro Ser Leu Trp Asp Arg Phe Ser Ser Ser Thr Ser Ser Se
1               5                   10                  15
```

-continued

```
Pro Ser Ser Leu Pro Arg Thr Pro Thr Pro Asp Arg Pro Pro Arg Se
            20                  25                  30

Ala Trp Gly Ser Ala Thr Arg Glu Glu Gly Phe Asp Arg Ser Thr Se
            35                  40                  45

Leu Glu Ser Ser Asp Cys Glu Ser Leu Asp Ser Ser Asn Ser Gly Ph
 50                  55                  60

Gly Pro Glu Glu Asp Thr Ala Tyr Leu Asp Gly Val Ser Leu Pro As
 65                  70                  75                  80

Phe Glu Leu Leu Ser Asp Pro Glu Asp Glu His Leu Cys Ala Asn Le
                 85                  90                  95

Met Gln Leu Leu Gln Glu Ser Leu Ala Gln Ala Arg Leu Gly Ser Ar
            100                 105                 110

Arg Pro Ala Arg Leu Leu Met Pro Ser Gln Leu Val Ser Gln Val Gl
            115                 120                 125

Lys Glu Leu Leu Arg Leu Ala Tyr Ser Glu Pro Cys Gly Leu Arg Gl
            130                 135                 140

Ala Leu Leu Asp Val Cys Val Glu Gln Gly Lys Ser Cys His Ser Va
145                 150                 155                 160

Gly Gln Leu Ala Leu Asp Pro Ser Leu Val Pro Thr Phe Gln Leu Th
                165                 170                 175

Leu Val Leu Arg Leu Asp Ser Arg Leu Trp Pro Lys Ile Gln Gly Le
            180                 185                 190

Phe Ser Ser Ala Asn Ser Pro Phe Leu Pro Gly Phe Ser Gln Ser Le
            195                 200                 205

Thr Leu Ser Thr Gly Phe Arg Val Ile Lys Lys Leu Tyr Ser Se
            210                 215                 220

Glu Gln Leu Leu Ile Glu Glu Cys
225                 230
```

(2) INFORMATION FOR SEQ ID NO: 11:

(i) SEQUENCE CHARACTERISTICS:
        (A) LENGTH: 864 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO: 11:

```
Met Ala Met Pro Leu Ser Arg Lys Asp Pro Thr Ser Asn Ala Ala As
 1               5                  10                  15

Gly Pro Leu Leu Lys Ala Ser Val Ser Ser Pro Val Lys Ala Ser Se
            20                  25                  30

Ser Pro Val Arg Ser Ala Pro Phe Ile Thr Arg Asn Cys Glu Val Gl
            35                  40                  45

Ser Pro Glu Leu Leu His Lys Thr Val Ser Pro Leu Lys Thr Glu Va
 50                  55                  60

Leu Lys Pro Cys Glu Lys Pro Thr Leu Ser Gln Ala Leu Gln Pro Ly
 65                  70                  75                  80

Glu Gly Ala Asn Lys Glu Val Cys Leu Gln Ser Gln Ser Lys Asp Ly
                 85                  90                  95

Leu Ala Thr Pro Gly Gly Arg Gly Ile Lys Pro Phe Leu Glu Arg Ph
            100                 105                 110

Gly Glu Arg Cys Gln Glu His Ser Lys Glu Ser Pro Thr Cys Arg Al
```

-continued

```
                115                 120                 125
Phe His Arg Thr Pro Asn Ile Thr Pro Asn Thr Lys Ala Ile Gln Gl
    130                 135                 140

Arg Leu Phe Lys Gln Asn Thr Cys Phe Ile Tyr Tyr Pro Asn Leu Al
145                 150                 155                 160

Gln Gln Leu Lys Gln Glu Arg Glu Lys Glu Leu Ala Cys Leu Arg Gl
                165                 170                 175

Arg Phe Asp Lys Gly Ser Leu Trp Ser Ala Glu Lys Asp Glu Lys Se
            180                 185                 190

Arg Ser Lys Gln Leu Glu Thr Asn Arg Lys Phe Thr Val Arg Thr Le
        195                 200                 205

Pro Ser Arg Asn Thr Lys Leu Ser Gln Gly Thr Pro Ser Thr Ser Va
    210                 215                 220

Ser Asp Lys Val Ala Glu Thr Pro Thr Ala Val Lys Ile Ser Gly Th
225                 230                 235                 240

Glu Pro Ala Gly Ser Thr Glu Ser Glu Met Thr Lys Ser Ser Pro Le
                245                 250                 255

Lys Ile Thr Leu Phe Leu Glu Glu Lys Ser Leu Lys Val Ala Se
            260                 265                 270

Asp Pro Glu Val Glu Gln Lys Thr Glu Ala Val His Glu Val Glu Me
        275                 280                 285

Ser Val Asp Asp Glu Asp Ile Asn Ser Ser Lys Ser Leu Thr Thr Se
    290                 295                 300

Ser Val Xaa Ser Leu Xaa Glu Xaa Gly Thr Gly Xaa Trp Lys Arg Xa
305                 310                 315                 320

Lys Glu Glu Met Asp Gln Val Gly Asn Gly Lys Gln Arg Gly Ala Gl
                325                 330                 335

Arg Cys Ala Glu Tyr Leu Leu Asn Xaa Xaa Thr Xaa Ser Arg Trp Le
            340                 345                 350

Arg Arg Phe Gly Val Val Asn Leu Gln Asn Val Ile Ser Ser Pro Gl
        355                 360                 365

Leu Glu Leu Arg Asp Tyr Ser Leu Ser Ala Pro Ser Pro Lys Pro Gl
    370                 375                 380

Lys Phe Gln Arg Thr Arg Val Pro Arg Ala Glu Ser Gly Asp Ser Le
385                 390                 395                 400

Ser Ser Glu Asp Arg Asp Leu Leu Tyr Ser Ile Asp Ala Tyr Arg Se
                405                 410                 415

Gln Arg Phe Lys Glu Thr Glu Arg Pro Ser Ile Lys Gln Val Ile Va
            420                 425                 430

Arg Lys Glu Asp Val Thr Ser Lys Leu Ser Glu Lys Asn Gly Val Ph
        435                 440                 445

Ser Gly Gln Val Asn Ile Lys Gln Lys Met Gln Glu Leu Asn As
    450                 455                 460

Ile Asn Leu Gln Gln Thr Val Ile Tyr Gln Ala Ser Gln Ala Leu As
465                 470                 475                 480

Cys Cys Val Asp Glu Glu His Gly Lys Gly Ser Leu Glu Glu Ala Gl
                485                 490                 495

Ala Glu Arg Leu Phe Leu Xaa Ala Thr Glu Lys Arg Ala Leu Leu Il
            500                 505                 510

Asp Glu Leu Asn Lys Leu Lys Ser Glu Gly Pro Gln Arg Arg Asn Ly
        515                 520                 525

Thr Ala Val Ala Ser Gln Ser Gly Phe Ala Pro Cys Lys Gly Ser Va
    530                 535                 540
```

```
Thr Leu Ser Glu Ile Cys Leu Pro Leu Lys Ala Glu Phe Val Cys Se
545                 550                 555                 560

Thr Ala Gln Lys Pro Glu Ser Ser Asn Tyr Tyr Tyr Leu Ile Met Le
                565                 570                 575

Lys Ala Gly Ala Glu Gln Met Val Ala Thr Pro Leu Ala Ser Thr Al
                580                 585                 590

Thr Leu Leu Val Val Met Xaa Leu Thr Phe Pro Thr Thr Leu Pro Xa
                595                 600                 605

Xaa Asp Val Ser Asn Asp Phe Glu Ile Asn Val Glu Val Tyr Ser Le
        610                 615                 620

Val Gln Lys Lys Asp Ser Leu Arg Pro Glu Lys Lys Lys Ala Se
625                 630                 635                 640

Lys Phe Lys Ala Ile Thr Pro Lys Arg Leu Leu Thr Ser Ile Thr Se
                645                 650                 655

Lys Ser Ser Leu His Ala Ser Val Met Ala Ser Pro Gly Gly Leu Se
                660                 665                 670

Ala Val Arg Thr Ser Asn Phe Thr Leu Val Gly Ser His Thr Leu Se
                675                 680                 685

Leu Ser Ser Val Gly Asp Thr Lys Phe Ala Leu Asp Lys Val Pro Ph
690                 695                 700

Leu Ser Pro Leu Glu Gly His Ile Cys Leu Lys Ile Ser Cys Gln Va
705                 710                 715                 720

Asn Ser Ala Val Glu Glu Lys Gly Phe Leu Thr Ile Phe Glu Asp Va
                725                 730                 735

Ser Gly Phe Gly Ala Trp His Arg Arg Trp Cys Val Leu Ser Gly As
                740                 745                 750

Cys Ile Ser Tyr Trp Thr Tyr Pro Asp Asp Glu Arg Arg Lys Asn Pr
                755                 760                 765

Ile Gly Arg Ile Asn Leu Ala Asn Cys Ile Ser His Gln Ile Glu Pr
770                 775                 780

Ala Asn Arg Glu Phe Cys Ala Arg Arg Asn Thr Leu Glu Leu Ile Th
785                 790                 795                 800

Val Arg Pro Gln Arg Glu Asp Asp Arg Glu Thr Leu Val Ser His Va
                805                 810                 815

Glu Thr His Ser Val Ser Pro Lys Asn Trp Leu Ser Ala Asp Thr Ly
                820                 825                 830

Glu Glu Arg Asp Leu Trp Met Gln Lys Leu Asn Gln Val Ile Val As
                835                 840                 845

Ile Arg Leu Trp Gln Pro Asp Ala Cys Tyr Lys Pro Val Gly Lys Pr
850                 855                 860
```

What is claimed is:

1. An isolated polypeptide having an amino acid sequence selected from the group consisting of SEQ ID NO:9 and SEQ ID NO:10.

2. An isolated polypeptide in accordance with claim 1 having the amino acid sequence of SEQ ID NO:9.

3. An isolated polypeptide in accordance with claim 1 having the amino acid sequence of SEQ ID NO:10.

* * * * *